US012583097B2

(12) United States Patent
Kawakami et al.

(10) Patent No.: US 12,583,097 B2
(45) Date of Patent: Mar. 24, 2026

(54) INSERTION INSTRUMENT

(71) Applicant: OLYMPUS MEDICAL SYSTEMS CORP., Tokyo (JP)

(72) Inventors: Takumi Kawakami, Tachikawa (JP); Ryo Hasegawa, Hachioji (JP); Eijiro Sato, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 521 days.

(21) Appl. No.: 18/089,784

(22) Filed: Dec. 28, 2022

(65) Prior Publication Data

US 2023/0219212 A1     Jul. 13, 2023

Related U.S. Application Data

(60) Provisional application No. 63/298,684, filed on Jan. 12, 2022.

(51) Int. Cl.
    *A61B 1/005*       (2006.01)
    *A61B 1/00*        (2006.01)
           (Continued)

(52) U.S. Cl.
    CPC ............... *B25J 1/02* (2013.01); *A61B 1/0052* (2013.01); *A61B 1/0057* (2013.01); *F16C 1/106* (2013.01); *G02B 23/2476* (2013.01)

(58) Field of Classification Search
    CPC . A61B 1/0052; A61B 1/0057; A61B 1/00066; A61B 1/00105; F16C 1/12; A61M 25/0136
    See application file for complete search history.

(56) References Cited

U.S. PATENT DOCUMENTS

2003/0092965 A1*   5/2003   Konomura ........... A61B 1/0016
                                             600/152
2016/0192823 A1*   7/2016   Yasunaga ........... A61B 1/00042
                                             600/109
(Continued)

FOREIGN PATENT DOCUMENTS

JP       2016-055041 A      4/2016
JP       2017-012300 A      1/2017
(Continued)

*Primary Examiner* — Anh Tuan T Nguyen
*Assistant Examiner* — Rynae E Boler
(74) *Attorney, Agent, or Firm* — Morgan, Lewis & Bockius LLP

(57)            ABSTRACT

An insertion instrument comprises an insertion portion including a bending portion provided at a distal end side of the insertion portion, a first wire provided in the insertion portion, and an operation portion provided at a proximal end side of the insertion portion. The operation portion includes a bending operation unit. The bending operation unit includes a lever having a central shaft defining a central axis, a rotor coupled to the lever, a wire attachment surface to which the first wire is attached. An inner surface of the operation portion includes a receiver body and a restriction body. The receiver body supports the rotor for rotation about the central axis and for movement of the lever from a neutral position to an inclined position, where, in the inclined position, the central shaft is inclined relative to the central shaft in the neutral position. Movement of the lever from the neutral position to the inclined position pulls the first wire to bend the bending portion. The restriction surface restricts a portion of the rotation of the rotor about the central axis.

20 Claims, 47 Drawing Sheets

(51) Int. Cl.
    *A61M 25/01*      (2006.01)
    *B25J 1/02*       (2006.01)
    *F16C 1/10*       (2006.01)
    *G02B 23/24*     (2006.01)

(56)           References Cited

U.S. PATENT DOCUMENTS

| | | | |
|---|---|---|---|
| 2017/0196435 A1* | 7/2017 | Sato | G02B 23/24 |
| 2018/0049625 A1* | 2/2018 | Nakade | A61B 1/00 |
| 2019/0014972 A1 | 1/2019 | Hatano et al. | |
| 2019/0150706 A1* | 5/2019 | Matsui | A61B 1/00042 |
| 2020/0121165 A1* | 4/2020 | Nakao | A61B 1/0052 |

FOREIGN PATENT DOCUMENTS

| | | |
|---|---|---|
| JP | 6058247 B1 | 1/2017 |
| JP | 6234649 B1 | 11/2017 |
| JP | 6506890 B1 | 4/2019 |
| WO | 2016/167099 A1 | 10/2016 |

* cited by examiner

INSERTION INSTRUMENT

RELATED APPLICATION DATA

This application is based on and claims priority under 35 U.S.C. § 119 to U.S. Provisional Application No. 63/298,684 filed on Jan. 12, 2022, the entire contents of which are incorporated herein by reference.

FIELD OF THE DISCLOSURE

The present disclosure relates to an insertion instrument including a bending portion configured to bend in cooperation with a tilt operation of a bending operation lever.

BACKGROUND

Conventionally, an insertion instrument such as an endoscope has been widely used in medical and industrial fields. An endoscope as an example of the insertion instrument typically includes a bending portion on a distal end side of an insertion portion. The bending portion is configured to be bendable in accordance with a hand-side operation by a user.

A configuration including a joystick-type bending operation lever as a bending operation mechanism for performing a bending operation on such a bending portion has been known. The joystick-type bending operation lever is tiltable in all directions including up, down, right, and left directions. Thus, in this kind of bending operation mechanism, the bending portion can be bent in all directions including the up, down, right, and left directions with a single mechanism.

For example, Japanese Patent Application Laid-Open Publication No. 2016-55041 discloses, as a configuration of the bending operation mechanism in which the bending operation lever is tiltable in all directions, a configuration including a ball joint at which a sphere provided at a rod of a joystick lever (bending operation lever) is fitted to a sphere receiver provided at a housing (outer shell). For example, Japanese Patent No. 6506890 discloses a configuration in which a fixation member coupled to the bending operation lever is supported to a housing through two rotation shafts orthogonal to each other.

SUMMARY OF THE DISCLOSURE

An insertion instrument comprises an insertion portion including a bending portion provided at a distal end side of the insertion portion, a first wire provided in the insertion portion, and an operation portion provided at a proximal end side of the insertion portion. The operation portion includes a bending operation unit. The bending operation unit includes a lever having a central shaft defining a central axis, a rotor coupled to the lever, a wire attachment surface to which the first wire is attached. An inner surface of the operation portion includes a receiver body and a restriction body. The receiver body supports the rotor for rotation about the central axis and for movement of the lever from a neutral position to an inclined position, where, in the inclined position, the central shaft is inclined relative to the central shaft in the neutral position. Movement of the lever from the neutral position to the inclined position pulls the first wire to bend the bending portion. The restriction body restricts a portion of the rotation of the rotor about the central axis.

DETAILED DESCRIPTION

Figure 1:
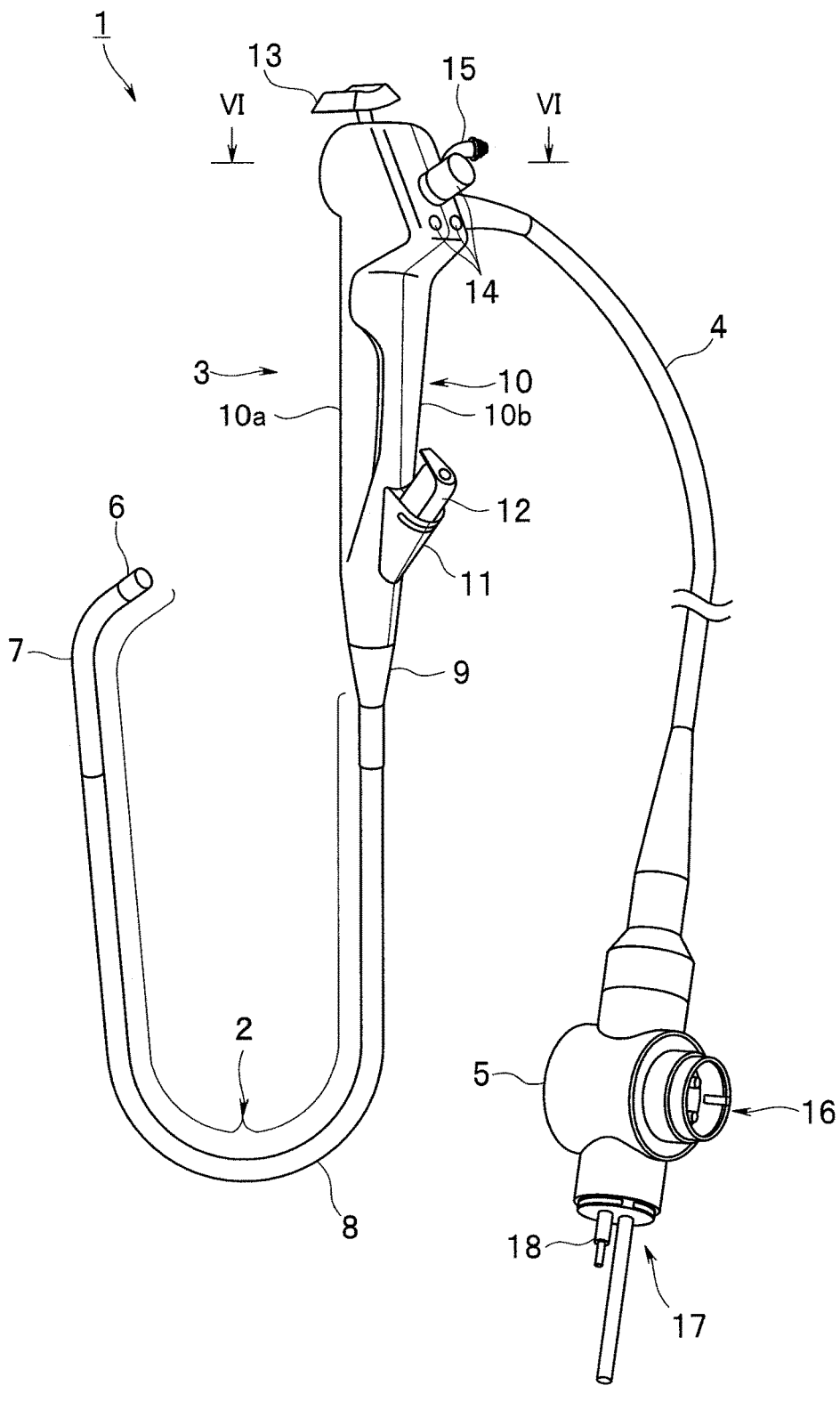
FIG. 1 relates to an embodiment of the present disclosure and is a perspective view illustrating a schematic configuration of an endoscope.

In a typical bending operation mechanism in which a bending operation lever is supported to a housing by using a ball joint or the like, the bending operation lever can rotate about a shaft of the bending operation lever. Thus, when a user tilts the bending operation lever, the bending operation lever rotates and operability degrades in some cases. However, a bending operation mechanism in which a bending operation lever is supported to a housing through two rotation shafts orthogonal to each other suffers increase in the number of components and tends to have a complicated structure.

According to an embodiment described below, it is possible to prevent rotation of a bending operation lever about a shaft with a simple configuration.

The embodiment will be described below with reference to FIGS. 1 to 24. Note that although a configuration of an endoscope as an example of an insertion instrument will be described in the present embodiment, other examples of the insertion instrument include a catheter and a forceps device that include a bending operation mechanism. Each drawing used in the following description is schematically illustrated, and dimensional relations, scaling, and the like among members are illustrated differently for each constituent component in some cases to indicate the respective constituent component in an enough size to allow recognition on the drawing. Thus, in the present disclosure, for example, the number of respective constituent components illustrated in each drawing, a shape of each constituent component, a size ratio of the respective constituent components, and a relative positional relation among the respective constituent components are not limited to illustrated forms.

An entire schematic configuration of an endoscope to which a bending operation mechanism according to the embodiment is applied will be first described below with reference to FIG. 1 before description of a detailed configuration of the bending operation mechanism.

An endoscope 1 of the present embodiment is, for example, an endoscope intended for urinary organs, digestive organs, respiratory organs, and circulatory organs. Furthermore, the endoscope 1 of the present embodiment is, for example, a single-use instrument that is discarded once inserted into an examination target body for a single examination.

The endoscope 1 includes an insertion portion 2, an operation portion 3, a universal cord 4, and an endoscope connector 5.

The insertion portion 2 is a tubal member formed in an elongated pipe shape and inserted into a subject. The insertion portion 2 includes, sequentially from a distal end side, a distal end portion 6, a bending portion 7, and a flexible tube portion 8, which are continuously provided. The insertion portion 2 has flexibility as a whole. The bending portion 7 is provided at a distal end side of the insertion portion 2.

Among the above-described components, the distal end portion 6 includes an image pickup unit that is an image pickup apparatus including an image pickup device inside, and an illumination unit or the like configured to forwardly emit illumination light (neither illustrated).

Note that a form of the endoscope 1 to which the present disclosure can be applied is not limited to the above-described example (electronic endoscope including an image pickup unit). For example, the form of the endoscope 1 may be what is called a fiber scope in a form that includes no image pickup unit and in which an image guide fiber is disposed at the insertion portion 2.

The bending portion 7 is configured to be able to actively bend upon reception of an inclination operation of a bending operation lever 13 provided at the operation portion 3. More specifically, the bending portion 7 is configured to be able to bend in all directions about a shaft of the insertion portion 2, the directions including four directions along an up-down direction and a right-left direction that is a direction intersecting the up-down direction. The up-down direction and the right-left direction in the endoscope 1 of the present embodiment are defined in association with an up-down direction and a right-left direction of an image picked up by the image pickup unit.

Figure 7:
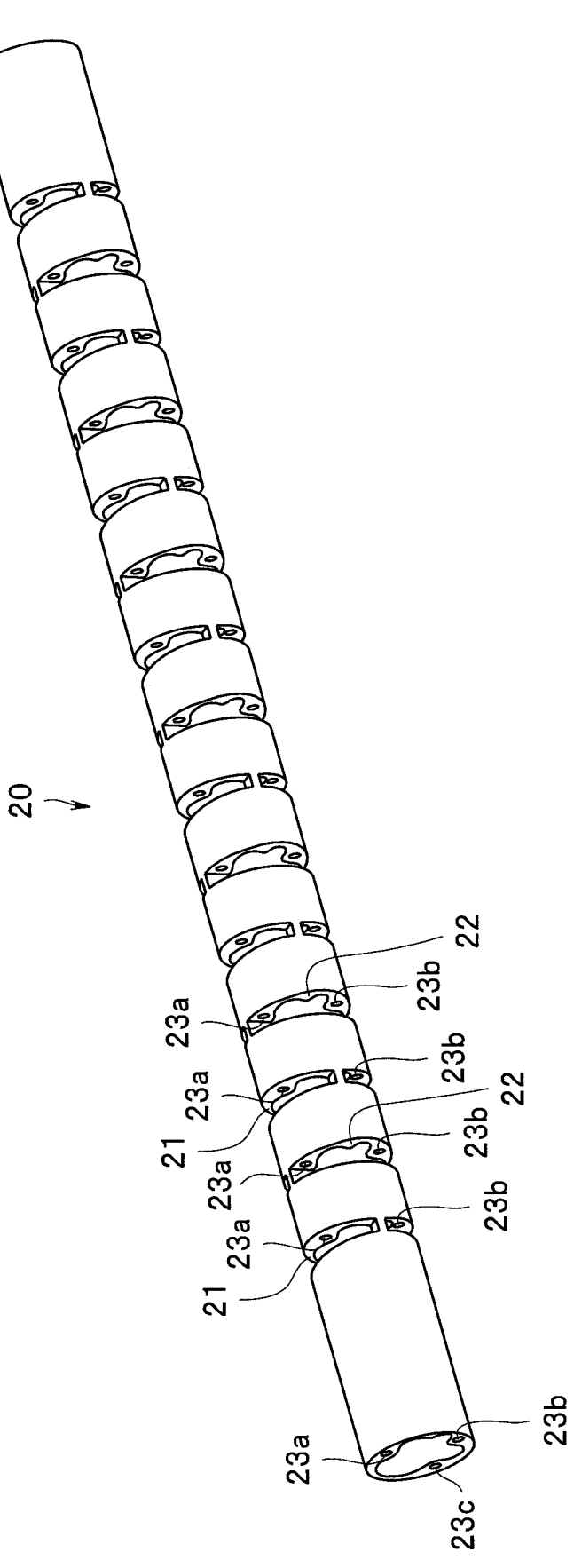
FIG. 7 relates to the embodiment of the present disclosure and is a perspective view illustrating a bending pipe.
Figure 8:
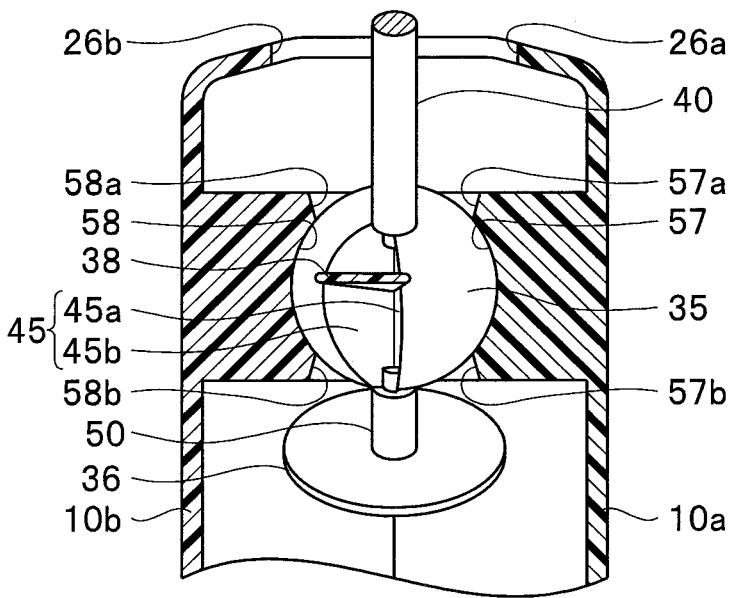
FIG. 8 relates to the embodiment of the present disclosure and is a main-part cross-sectional view illustrating the bending operation mechanism from a back surface side when a bending operation lever is at a neutral position.
Figure 9:
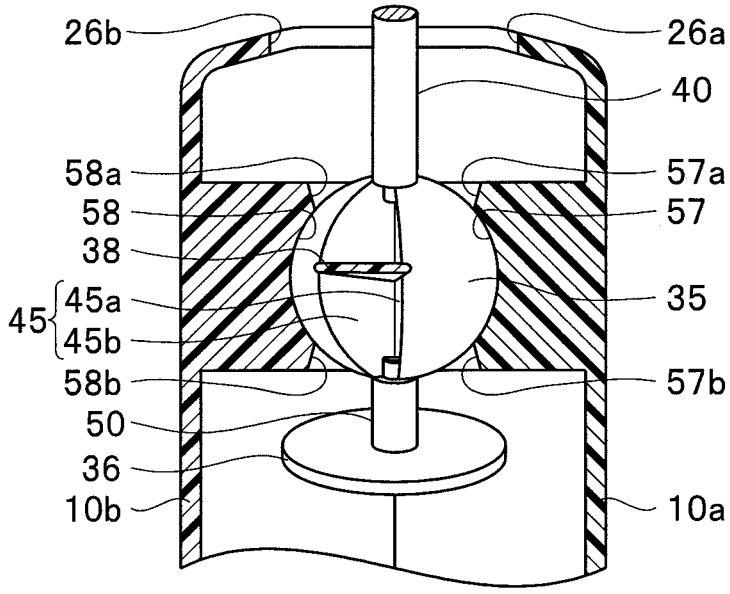
FIG. 9 relates to the embodiment of the present disclosure and is a main-part cross-sectional view illustrating the bending operation mechanism from the back surface side when the bending operation lever is inclined in an upward bending direction.
Figure 10:
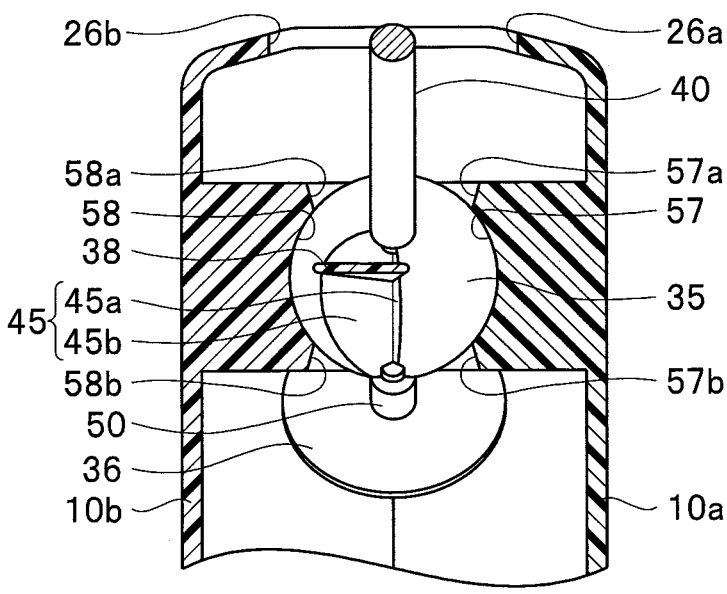
FIG. 10 relates to the embodiment of the present disclosure and is a main-part cross-sectional view illustrating the bending operation mechanism from the back surface side when the bending operation lever is inclined in a downward bending direction.
Figure 11:
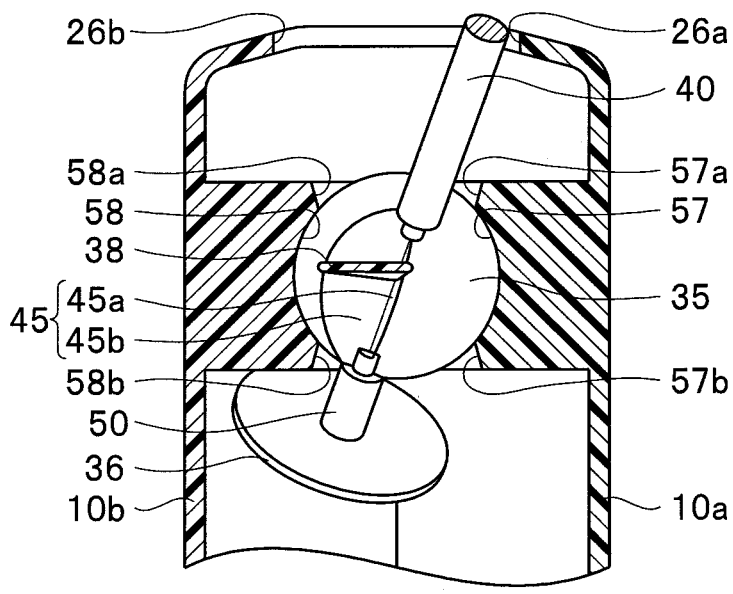
FIG. 11 relates to the embodiment of the present disclosure and is a main-part cross-sectional view illustrating the bending operation mechanism from the back surface side when the bending operation lever is inclined in a rightward bending direction.
Figure 12:
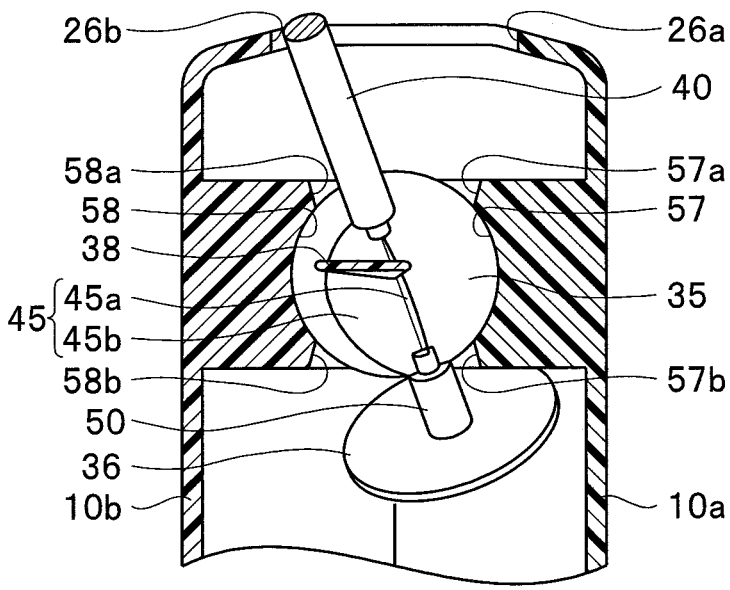
FIG. 12 relates to the embodiment of the present disclosure and is a main-part cross-sectional view illustrating the bending operation mechanism from the back surface side when the bending operation lever is inclined in a leftward bending direction.

To achieve such a bending operation, a bending pipe 20 is provided inside the insertion portion 2. For example, as illustrated in FIG. 7, first slits 21 paired in the up-down direction and second slits 22 paired in the right-left direction are alternately formed in a longitudinal axis direction in the bending pipe 20.

In addition, in the bending pipe 20, a plurality of wire insertion holes 23 (for example, first, second, third wire insertion holes 23a, 23b, and 23c) are provided in the longitudinal axis direction. First, second, and third bending wires 25a, 25b, and 25c (to be described later) that are wires are inserted into the first, second, third wire insertion holes 23a, 23b, and 23c, respectively. Distal end sides of the first, second, and third bending wires 25a, 25b, and 25c are fixed at a distal end side of the bending pipe 20. Accordingly, when one or two bending wires are pulled and the other bending wires are loosened, the bending pipe 20 (bending portion 7) bends in a predetermined direction in accordance with the pulled amounts of the bending wires. The first, second and third bending wire 25a, 25b and 25c are provided in the insertion portion 2.

The flexible tube portion 8 is a tubal member formed with bendability such that the member is passively flexible. A treatment instrument insertion channel, various electric signal lines extended from the image pickup unit, a light guide that guides the illumination light, and the like (none of them illustrated) are inserted inside the flexible tube portion 8.

The operation portion 3 is continuously provided on a proximal end side of the insertion portion 2 through a bend preventing portion 9. A housing (outer shell) 10 of the operation portion 3 includes a first outer shell 10a and a second outer shell 10b. In the present embodiment, the first outer shell 10a and the second outer shell 10b are divided on right and left sides in the longitudinal axis direction of the operation portion 3. The first outer shell 10a and the second outer shell 10b are bonded to each other, thereby forming an outer surface of the operation portion 3. The operation portion 3 is provided at a proximal end side of the insertion portion 2, and the operation portion 3 includes a bending operation unit. The first outer shell 10a forms a first portion of the outer surface of the operation portion 3, and a second outer shell 10b bonded to the first outer shell 10a and forming a second portion of the outer surface of the operation portion 3. At least one of the first outer shell 10a and the second outer shell 10b includes the restriction body 38. At least one of the first outer shell 10a and the second outer shell 10b includes the receiver body 37.

The operation portion 3 is provided with, for example, a treatment instrument insertion portion 11, the bending operation lever 13 as a lever, a plurality of operation buttons 14, and a suction valve 15.

The treatment instrument insertion portion 11 has a treatment instrument insertion opening (not illustrated) for inserting various treatment instruments (not illustrated). The treatment instrument insertion portion 11 communicates with the treatment instrument insertion channel inside the operation portion 3. Note that a forceps plug 12 for blocking the treatment instrument insertion opening can be removably attached to the treatment instrument insertion portion 11.

The bending operation lever 13 is configured to be able to incline in all directions including the up-down direction and the right-left direction set to the operation portion 3. The bending operation lever 13 is included in a bending operation mechanism 30 (see FIG. 2) to be described later. The bending operation mechanism 30 selectively pulls or loosens the bending wires 25 (first to third bending wires 25a to 25c) in accordance with an inclination state of the bending operation lever 13. Accordingly, a user can bend the bending portion 7 through an inclination operation on the bending operation lever 13.

Various kinds of functions of the endoscope 1 can be allocated to the plurality of operation buttons 14. For example, functions for performing an air-water feeding operation and a suction operation and functions for performing respective operations corresponding to the image pickup unit, the illumination unit, and the like can be allocated to the operation buttons 14.

The suction valve 15 is a coupling portion for coupling a suction pipeline to a non-illustrated suction device.

The universal cord 4 is a hollow tubal member having flexibility and extending from the operation portion 3. Various signal lines, a light guide, an air-water feeding tube, and the like extended from inside of the insertion portion 2 through inside of the operation portion 3 are inserted inside the universal cord 4.

The endoscope connector 5 is disposed at an extension end part of the universal cord 4. The endoscope connector 5 includes, for example, an electric connector portion 16 at a side surface part. The electric connector portion 16 can electrically connect a signal line inserted into the universal cord 4 to a processor (not illustrated) as an external instrument.

The endoscope connector 5 also includes a light source connector portion 17 and an air-water feeding plug 18 at a distal end surface. The light source connector portion 17 can optically connect a light guide inserted into the universal cord 4 to a light source device (not illustrated) as an external instrument. The air-water feeding plug 18 can connect the air-water feeding tube inserted into the universal cord to an air-water feeding device (not illustrated) as an external instrument.

Subsequently, a configuration of the bending operation mechanism 30 will be described in detail.

Figure 2:
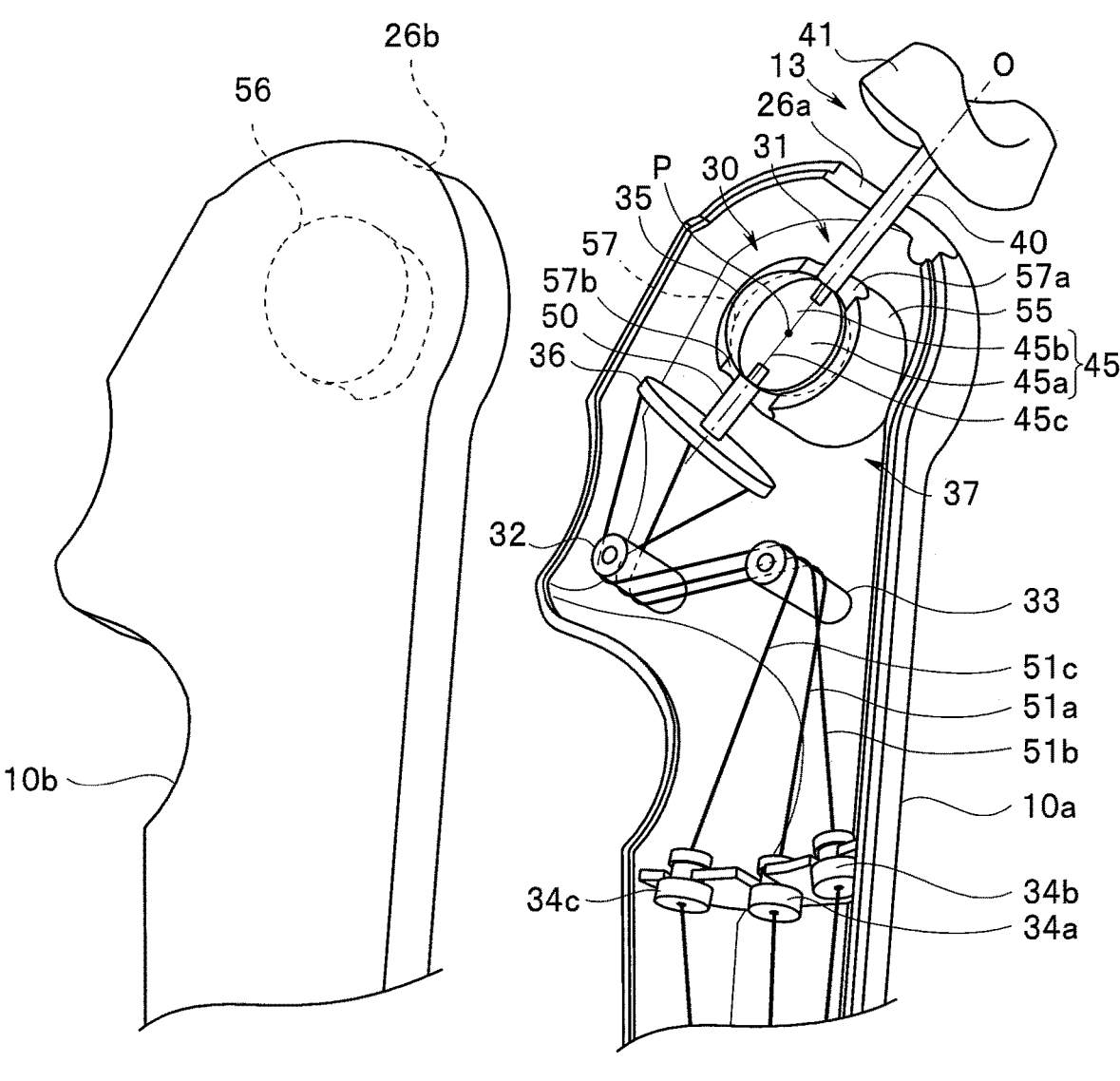
FIG. 2 relates to the embodiment of the present disclosure and is a perspective view illustrating a main part of a bending operation mechanism from which a second outer shell is removed.
Figure 3:
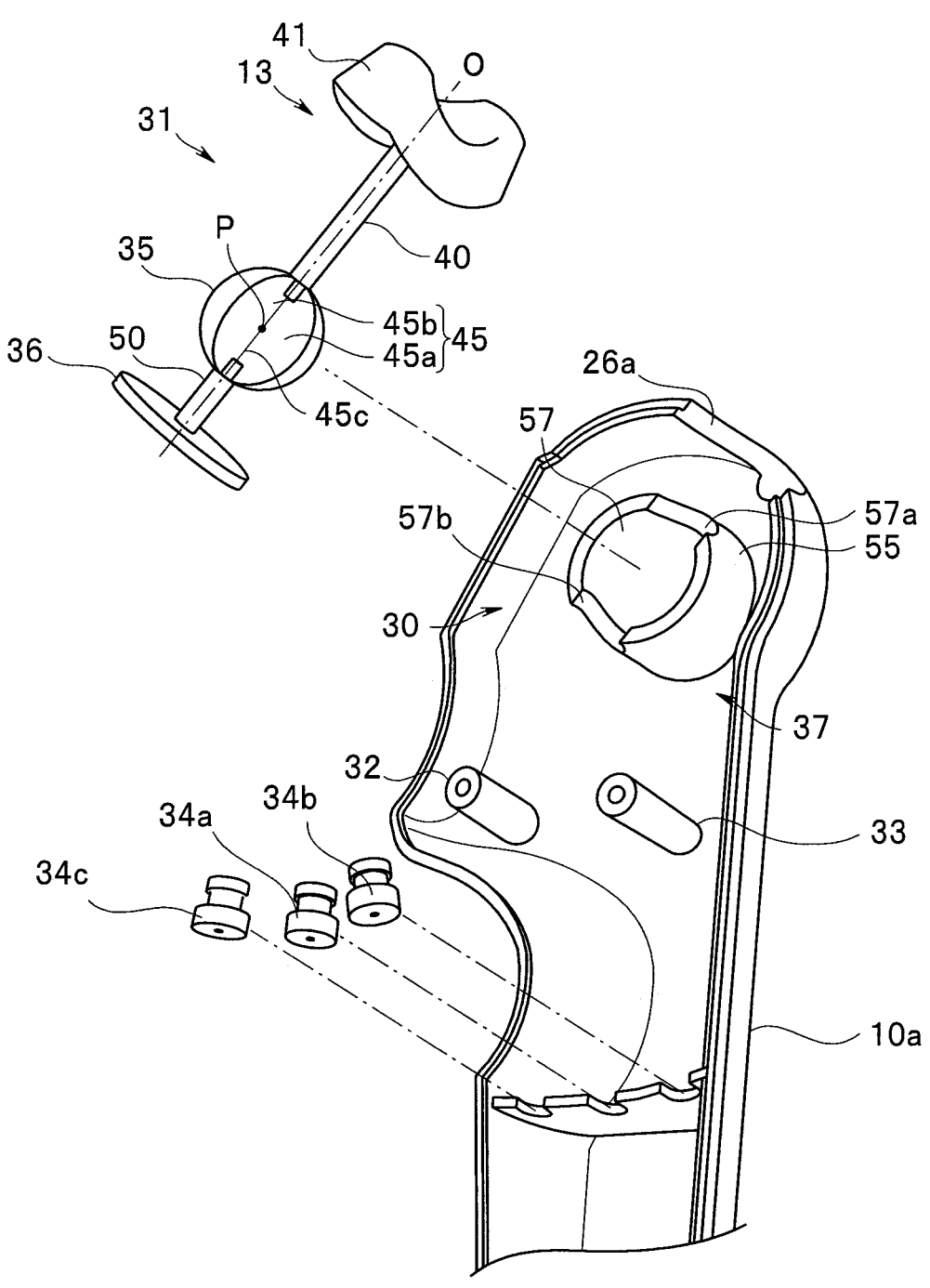
FIG. 3 relates to the embodiment of the present disclosure and is an exploded perspective view illustrating a main part of a first outer shell and the bending operation mechanism.
Figure 4:
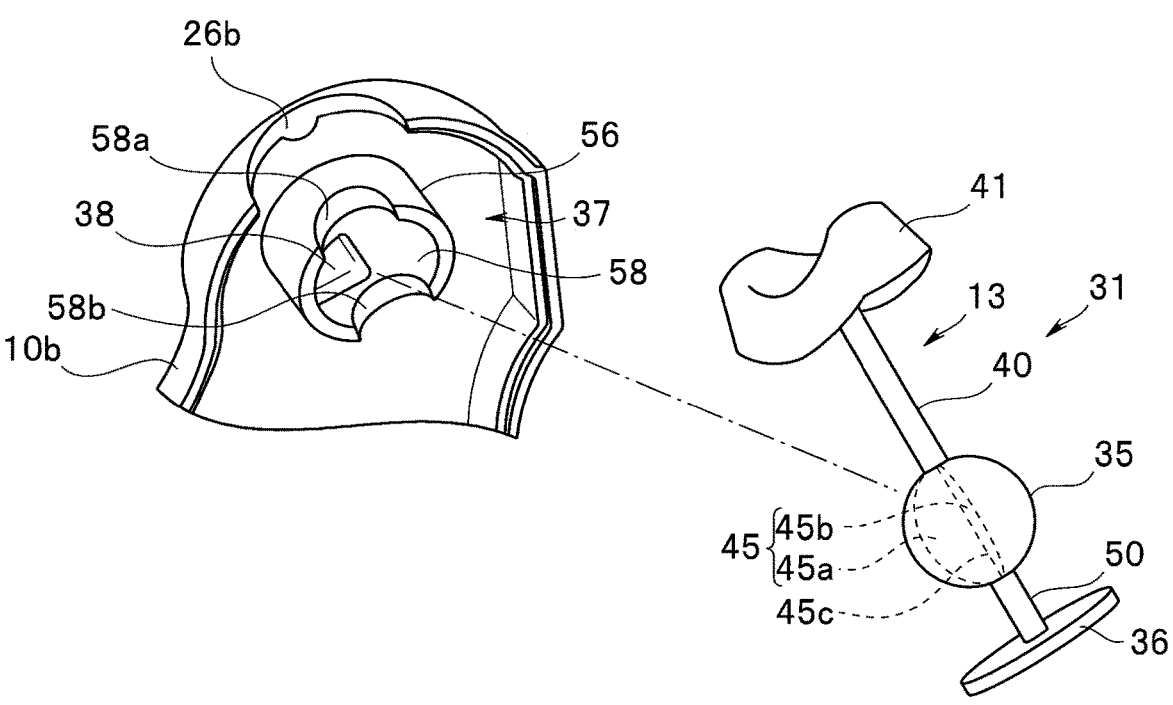
FIG. 4 relates to the embodiment of the present disclosure and is an exploded perspective view illustrating a main part of the second outer shell and the bending operation mechanism.

As illustrated in FIGS. 2 to 4, the bending operation mechanism 30 includes the above-described bending operation lever 13, a rotor 35, a wire fixation member 36 (or wire attachment surface), a support member 37 (or receiver body), and a restriction member 38 (or restriction body). Note that the bending operation lever 13 constitutes a bending operation unit 31 together with the rotor 35 and the wire fixation member 36.

The bending operation lever 13 includes a lever shaft 40 (or a central shaft) as a shaft and a finger placement member 41.

The lever shaft 40 is extended from inside of the operation portion 3 to outside of the operation portion 3 through an opening 26 provided at a proximal end of an outer shell 10. Note that, in the present embodiment, the opening 26 is formed as a combination of a first opening 26a provided at the first outer shell 10a, and a second opening 26b provided at the second outer shell 10b. The bending operation unit includes the lever 13 having a central shaft 40 defining a central axis O, the rotor 35 coupled to the lever 13, the wire attachment surface 36 to which the first bending wire 25a is attached, an inner surface of the operation portion includes a receiver body 37 and the restriction body 38. The receiver body 37 supports the rotor 35 for rotation about the central axis O and for movement of the lever 13 from a neutral position to an inclined position, where, in the inclined position, the central shaft 40 is inclined relative to the central shaft 40 in the neutral position. Movement of the lever 13 from the neutral position to the inclined position pulls the first wire 25a to bend the bending portion 7. The restriction body 38 restricts a portion of the rotation of the rotor 35 about the central axis O. The first, the second and the third bending wire 25a, 25b and 25c are attached to the wire attachment surface 36. The first wire, the second wire and the third bending wire 25a, 25b and 25c extend from the wire attachment surface 36 to the bending portion 7.

The finger placement member 41 is coupled to a proximal end of the lever shaft 40 outside the operation portion 3.

The rotor 35 is, for example, a rotation member having a basic shape of a sphere. A distal end of the lever shaft 40 of the bending operation lever 13 is coupled to the rotor 35.

A concave surface 45 is formed at a partial surface of the rotor 35. The concave surface 45 forms a recess. The concave surface 45 has the shape of a sphere from which a V-shaped part is cut out as illustrated in, for example, FIGS. 3 and 6. Accordingly, the concave part 45 includes a first plane part 45a and a second plane part 45b. The rotor 35 has a body including an outer peripheral surface and a recess 45, and the restriction body 38 extends into the recess 45. The restriction body 38 may extend toward a center P of the rotor 35.

An angle between the first plane part 45a and the second plane part 45b is set to, for example, 90°. A valley line 45c formed at intersection of the first plane part 45a and the second plane part 45b is set to, for example, a position passing through a center P of the rotor 35 and matching an extended line of a central axis O of the lever shaft 40. The recess 45 extends in a circumferential direction of the rotor 35 a first distance, the outer peripheral surface of the body extends in the circumferential direction of the rotor 35 a second distance. And the first distance may be equal to or less than the second distance. The first distance may be equal to or less than half the second distance.

Figure 5:
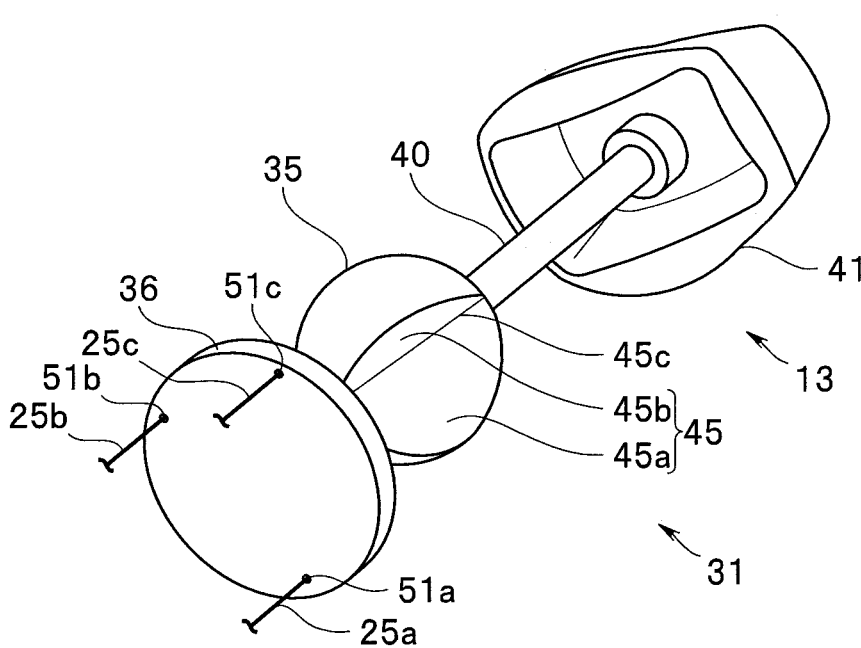
FIG. 5 relates to the embodiment of the present disclosure and is a perspective view illustrating a bending operation unit.

The wire fixation member 36 is made of a plate material having a disk shape as illustrated in, for example, FIGS. 3 to 5. A coupling shaft 50 is provided to extend from a central part of the wire fixation member 36. The coupling shaft 50 couples the wire fixation member 36 to the rotor 35 on the extended line of the central axis O of the lever shaft 40. With this coupling using the coupling shaft 50, the wire fixation member 36 is provided at a position different from the rotor 35 in a direction (longitudinal direction) of the central axis O of the lever shaft 40. The wire attachment surface 36 may have a shape of a plate, and a planar surface of the wire attachment surface 36 is orthogonal to the central axis O. The lever 13, the rotor 35, and the wire attachment surface 36 are arranged along the central axis O with the rotor 35 positioned between the lever 13 and the wire attachment surface 36.

As illustrated in FIG. 5, a plurality of wire fixation portions 51 (for example, first to third wire fixation portions 51a, 51b, and 51c) are provided at a marginal part of the wire fixation member 36. The first to third wire fixation portions 51a to 51c are, for example, through-holes provided at positions at an equal distance from a center of the wire fixation member 36. Proximal end sides of the first to third bending wires 25a to 25c are fixed to the first to third wire fixation portions 51a to 51c, respectively.

As illustrated in, for example, FIGS. 2 to 4, the support member 37 includes a first support member 55 provided on an inner surface of the first outer shell 10a, and a second support member 56 provided on an inner surface of the second outer shell 10b. Note that the first and second support members 55 and 56 are integrally formed with the first and second outer shells 10a and 10b.

The first support member 55 is formed as a protrusion having a substantially cylindrical shape. A shape of the first support member 55 that performs same function or movement as this disclosure is defined in the substantially cylindrical shape. A first spherical surface portion 57 having a concave partially spherical surface shape is formed at a tip part of the first support member 55. An inner diameter of the first spherical surface portion 57 is set to be slightly larger than an outer diameter of the rotor 35.

In addition, first and second communication grooves 57a and 57b for providing communication between inside of the first spherical surface portion 57 and a side part of the first support member 55 are provided at the tip part of the first support member 55. The first and second communication grooves 57a and 57b are, for example, grooves each having a circular arc shape and having an inner diameter sufficiently larger than an outer diameter of the lever shaft 40 and an outer diameter of the coupling shaft 50. The first and second communication grooves 57a and 57b are provided at positions facing each other through a central point of the first spherical surface portion 57.

The second support member 56 is formed as a protrusion having a substantially cylindrical shape. A shape of the second support member 56 that performs same function or movement as this disclosure is defined in the substantially cylindrical shape. The second support member 56 is provided at a position squarely facing the first support member 55 when the first outer shell 10a and the second outer shell 10b are bonded to each other.

A second spherical surface portion 58 (or surface of the receiver body) having a concave partially spherical surface shape is formed at a tip part of the second support member 56. An inner diameter of the second spherical surface portion 58 is set to be equal to the inner diameter of the first spherical surface portion 57. A central point of the second spherical surface portion 58 is set to a position that matches the central point of the first spherical surface portion 57 when the first outer shell 10a and the second outer shell 10b are bonded to each other. A surface of the receiver body 58 is curved, and the restriction body 38 may have a shape of a plate having a curved peripheral surface that contacts the surface of the receiver body 58. In a plane perpendicular to the central axis O, the restriction body 38 may have a wedge shape. The surface of the receiver body 58 is curved, and the outer surface the rotor 35 has a spherical shape contacting the surface of the receiver body 58.

In addition, third and fourth communication grooves 58a and 58b for providing communication between inside of the second spherical surface portion 58 and a side part of the second support member 56 are provided at the tip part of the second support member 56. The third and fourth communication grooves 58a and 58b are, for example, grooves each having a circular arc shape and having an inner diameter sufficiently larger than the outer diameter of the lever shaft 40 and the outer diameter of the coupling shaft 50. The third and fourth communication grooves 58a and 58b are provided at positions facing each other through the central point of the second spherical surface portion 58 and squarely facing the first and second communication grooves 57a and 57b, respectively.

The first and second support members 55 and 56 thus configured hold the rotor 35 between the first spherical surface portion 57 and the second spherical surface portion 58 when the first and second outer shells 10a and 10b are bonded to each other. Accordingly, at least part of the rotor 35 internally contacts the first and second spherical surface portions 57 and 58 in a slidable manner by surface contact. With this slidable internal contact, the rotor 35 is rotatably supported inside the operation portion 3.

In this state, the lever shaft 40 penetrates through the first and third communication grooves 57a and 58a, and the coupling shaft 50 penetrates through the second and fourth communication grooves 57b and 58b. As described above, the inner diameters of the first and third communication grooves 57a and 58a are set to be sufficiently larger than the outer diameter of the lever shaft 40. The inner diameters of the second and fourth communication grooves 57b and 58b are set to be larger than the outer diameter of the coupling shaft 50. Accordingly, the bending operation lever 13 and the wire fixation member 35 can incline relative to the support member 37 (first and second support members 55 and 56).

The restriction member 38 has, for example, a plate shape and is made of, for example, a tapered plate material having a substantially right triangular shape in a plan view. A shape of the restriction member 38 that performs same function or movement as this disclosure is defined in the substantially right triangular shape. The restriction member 38 has a shape for smooth contact with the concave surface 45 and has, for example, a curved surface curved in a thickness direction (see FIGS. 4 and 8 to 12). Note that the curved surface may have any other shape such as a chamfer shape as long as smooth contact with the concave surface 45 is possible.

Figure 6:
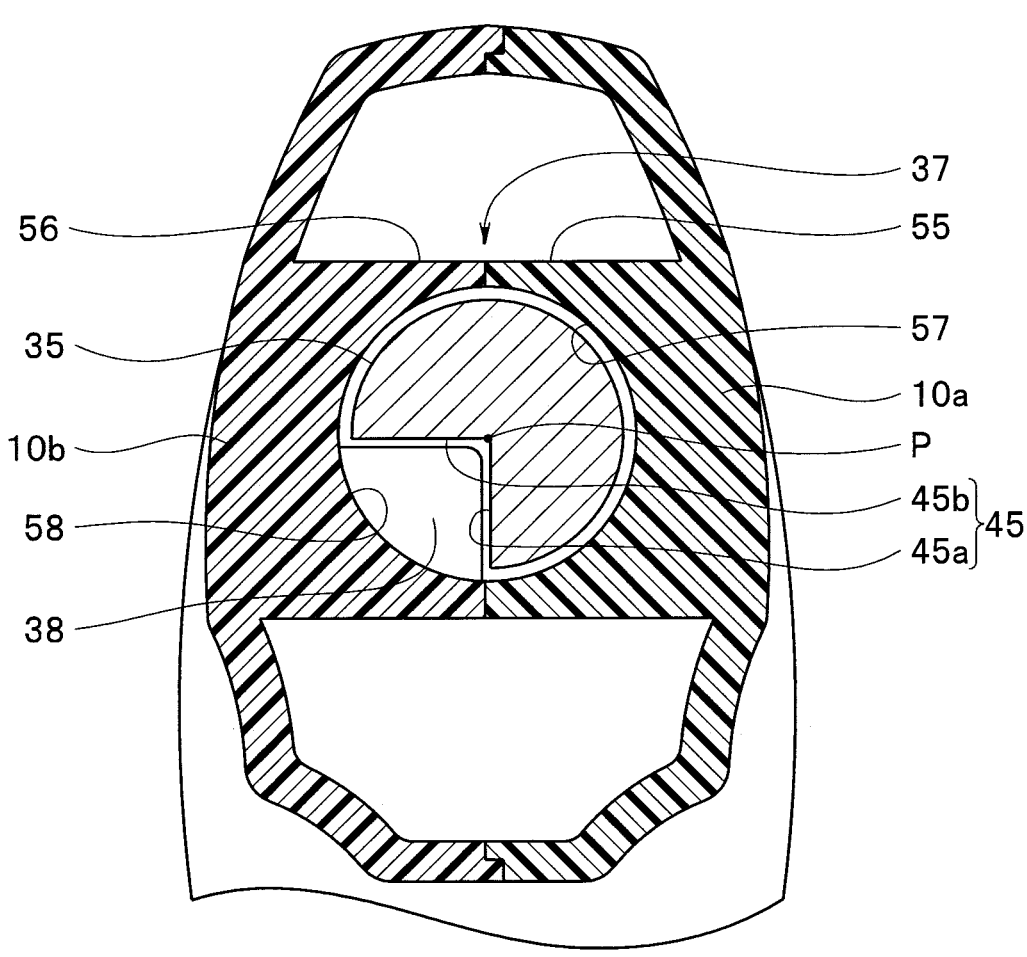
FIG. 6 relates to the embodiment of the present disclosure and is a VI-VI cross-sectional view of FIG. 1.

The restriction member 38 is integrally formed inside the first spherical surface portion 57 such that a distal end protrudes toward the central point of the first spherical surface portion 57 (see FIGS. 4 and 6). In other words, the restriction member 38 protrudes toward the central point P of the rotor 35 supported by the first and second support members 55 and 56. Note that the restriction member 38 is not limited to a component integrated with the first outer shell 10a and the second outer shell 10b. The restriction member 38 may be formed by attaching a separate member to the first outer shell 10a or the second outer shell 10b. Moreover, the distal end of the restriction member 38 is not limited to a configuration in which the distal end of the restriction member 38 is precisely directed to the central point of the first spherical surface portion 57. In other words, the distal end of the restriction member may be directed to a center of the rotor 35 with some width.

The restriction member 38 is inserted inside the concave surface 45 of the rotor when the rotor 35 is supported between the first and second spherical surface portions 57 and 58 (see FIG. 6). Accordingly, the restriction member 38 restricts rotation operation centered at the central axis O of the bending operation lever 13 (lever shaft 40) but allows inclination operation of the bending operation lever 13 (lever shaft 40) in all directions.

In other words, as illustrated in FIGS. 1 to 12, when the bending operation lever 13 is inclined, a relative positional relation between the central point P of the rotor 35 and the restriction member 38 is kept relative positions of the first and second plane parts 45a and 45b of the concave surface 45 and the restriction member 38 and an angle between each of the first and second plane parts 45a and 45b of the concave surface 45 and the restriction member 38 change. Accordingly, inclination operation of the bending operation lever 13 in all directions including the front-back direction and the right-left direction is allowed. When force in a rotational direction about the central axis O of the lever shaft 40 acts on the bending operation lever 13, any one of the first plane part 45a and the second plane part 45b contacts the restriction member 38. Accordingly, rotation operation of the bending operation lever 13 is restricted.

Figure 13:
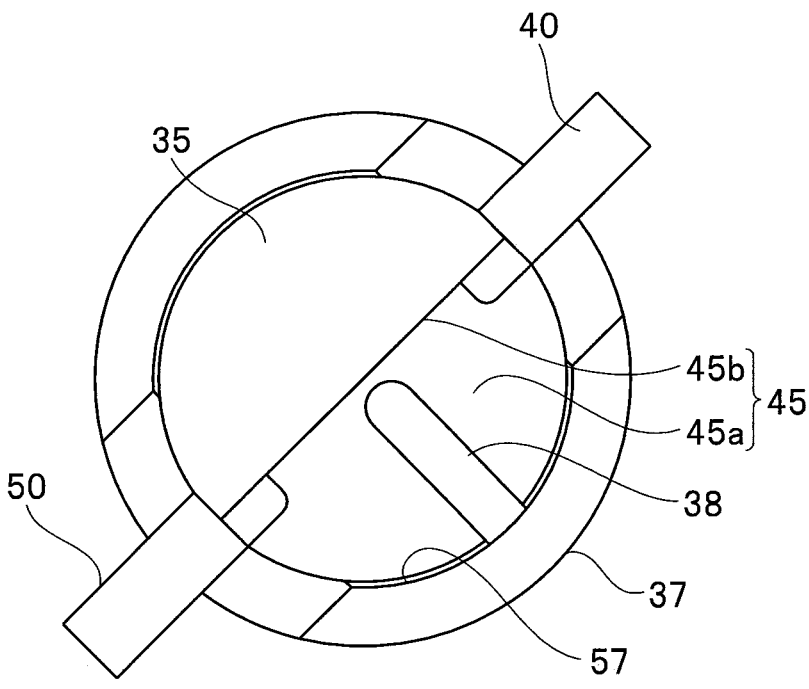
FIG. 13 relates to the embodiment of the present disclosure and is an explanatory diagram illustrating a relation between a concave surface and a restriction member when the bending operation lever is at the neutral position.
Figure 14:
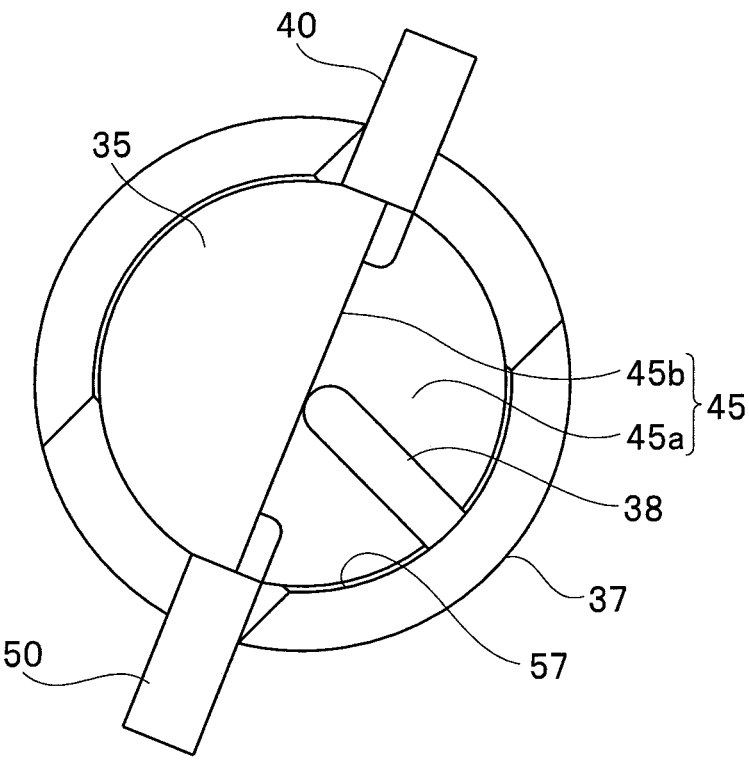
FIG. 14 relates to the embodiment of the present disclosure and is an explanatory diagram illustrating the relation between the concave surface and the restriction member when the bending operation lever is inclined in the downward bending direction.

Note that as illustrated in, for example, FIG. 13, the restriction member 38 is set to such a protrusion amount that a predetermined gap is formed between the restriction member 38 and the concave surface 45 of the rotor 35. This is for more reliable inclination operation of the bending operation lever 13. The gap vanishes by tilt operation of the bending operation lever 13 as illustrated in, for example, FIG. 14.

Figure 15:
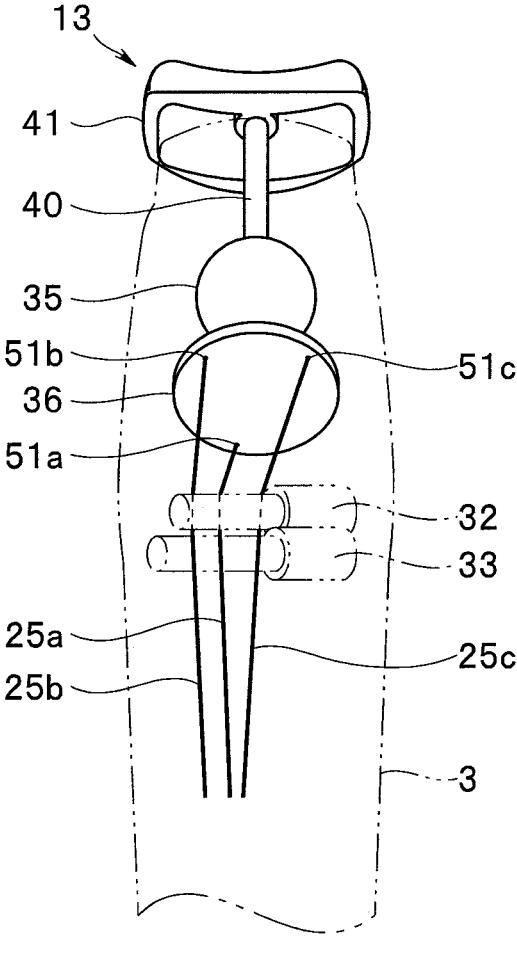
FIG. 15 relates to the embodiment of the present disclosure and is a front view illustrating a state of the bending operation unit and respective wires when the bending operation lever is at the neutral position.
Figure 16:
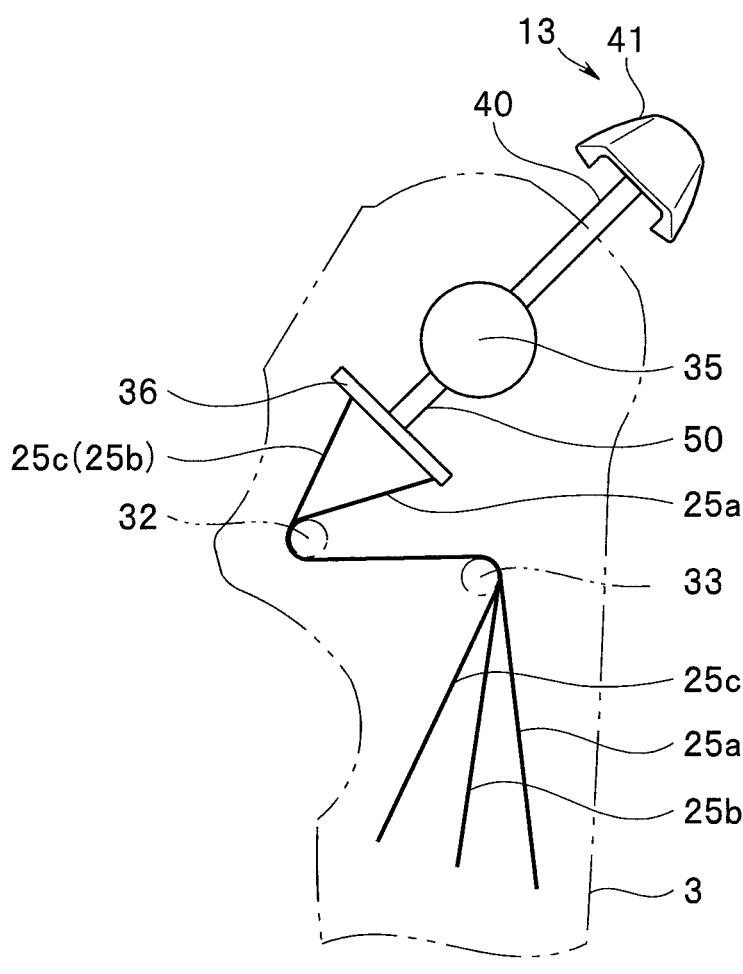
FIG. 16 relates to the embodiment of the present disclosure and is a left side view illustrating the state of the bending operation unit and the respective wires when the bending operation lever is at the neutral position.

As illustrated in, for example, FIGS. 2, 15, and 16, the first bending wire 25a is fixed on a lower side of the central axis O to the wire fixation member 36 that cooperates with the bending operation lever 13 through the rotor 35. The second and third bending wires 25b and 25c are fixed side by side on an upper side of the central axis O to the wire fixation member 36. Or the first bending wire 25a may be fixed on a closer side of one of first and second guide pins 32 and 33, the second and third bending wires 25b and 25c may be fixed side by side on a farther side of the one of first and second guide pins 32 and 33.

The first to third bending wires 25a to 25c extending from the wire fixation member 36 are guided to the insertion portion 2 side with extension directions of the first to third bending wires 25a to 25c changed by the first and second guide pins 32 and 33 protruding from the inner surface of the first outer shell 10a. Note that, in the present embodiment, the first and second guide pins 32 and 33 are also used as screwing bosses when the first outer shell 10a and the second outer shell 10b are bonded to each other.

The first to third bending wires 25a to 25c guided to the insertion portion 2 side are inserted into first to third wire guides 34a to 34c held by the first outer shell 10a and then inserted into the insertion portion 2.

Subsequently, bending operation of the endoscope 1 in which the first to third bending wires 25a to 25c are disposed inside the operation portion 3 as described above will be described.

Figure 17:
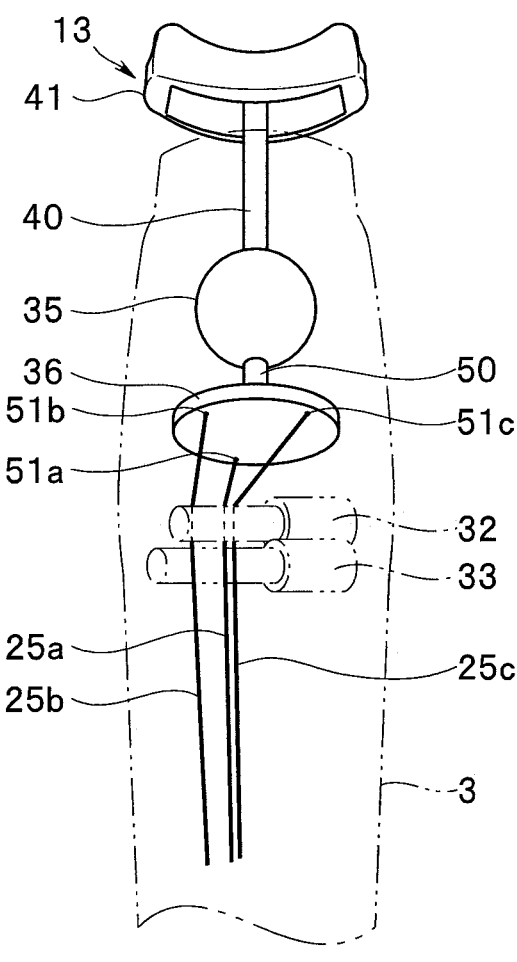
FIG. 17 relates to the embodiment of the present disclosure and is a front view illustrating the state of the bending operation unit and the respective wires when the bending operation lever is inclined in the upward bending direction.
Figure 18:
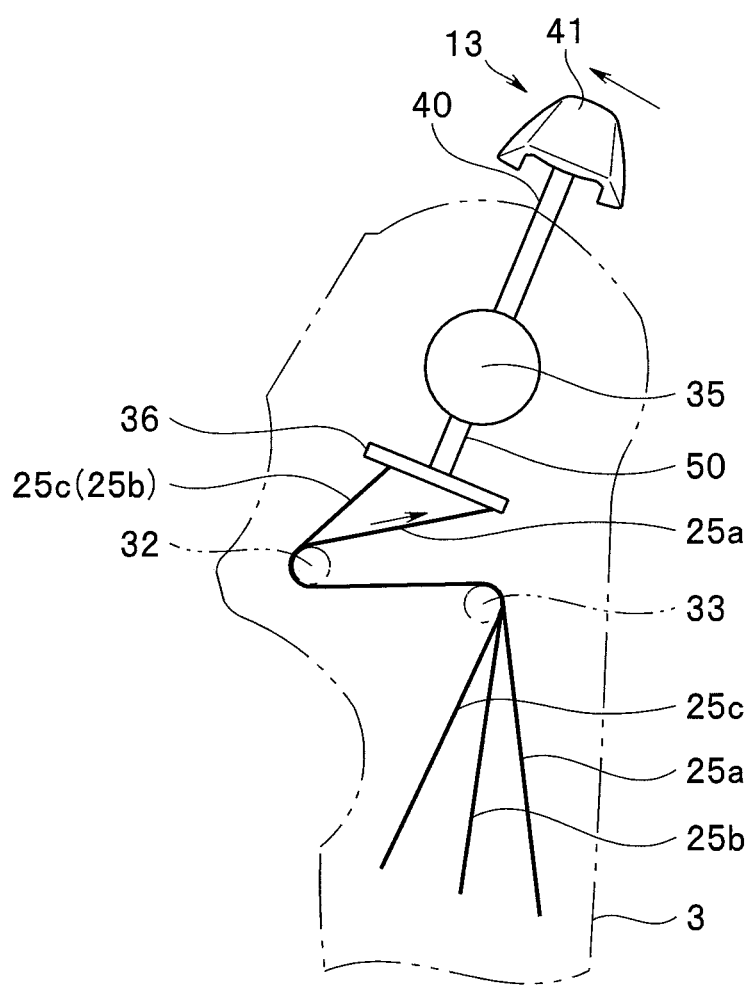
FIG. 18 relates to the embodiment of the present disclosure and is a left side view illustrating the state of the bending operation unit and the respective wires when the bending operation lever is inclined in the upward bending direction.

As illustrated in, for example, FIGS. 17 and 18, when the bending operation lever 13 is inclined in the up direction, the first bending wire 25a is pulled and the second and third bending wires 25b and 25c are loosened. Then, the bending portion 7 is bent in the up direction by pulling force of the first bending wire 25a. In this case, since rotation operation centered at the central axis O of the lever shaft 40 is restricted by the restriction member 38, a bending operation (inclination operation) by the user is accurately transferred to the wire fixation member 36.

Figure 19:
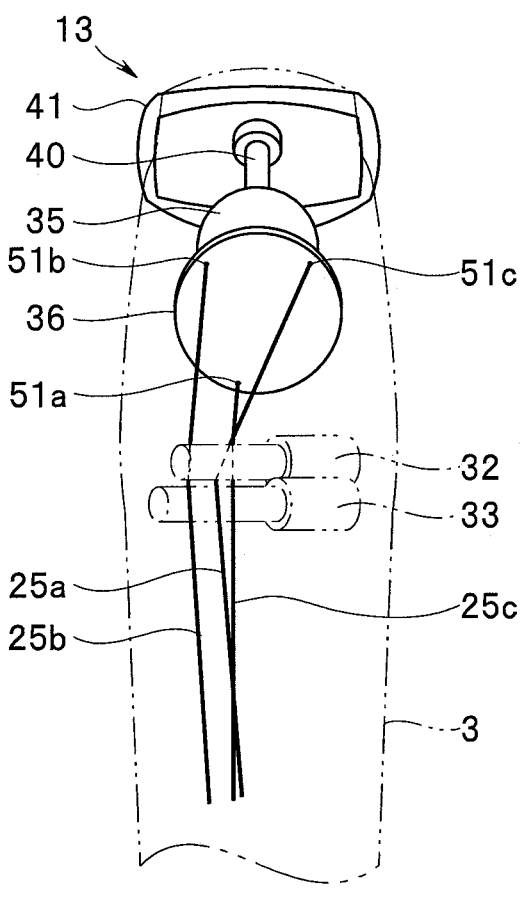
FIG. 19 relates to the embodiment of the present disclosure and is a front view illustrating the state of the bending operation unit and the respective wires when the bending operation lever is inclined in the downward bending direction.
Figure 20:
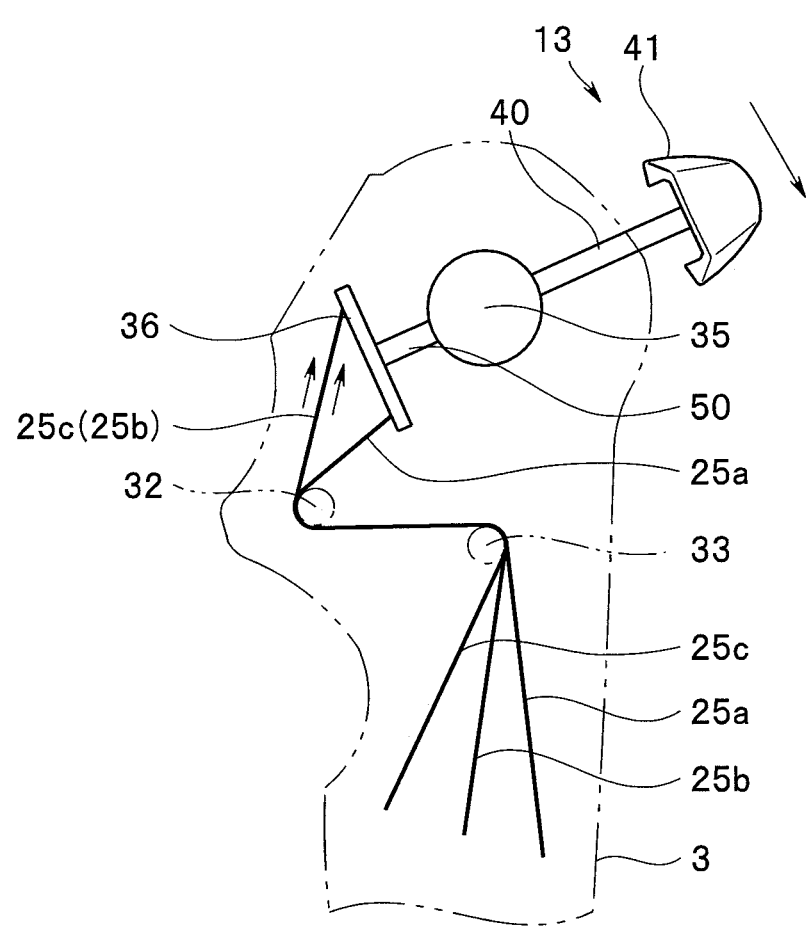
FIG. 20 relates to the embodiment of the present disclosure and is a left side view illustrating the state of the bending operation unit and the respective wires when the bending operation lever is inclined in the downward bending direction.

As illustrated in, for example, FIGS. 19 and 20, when the bending operation lever 13 is inclined in the down direction, the second and third bending wires 25b and 25c are pulled and the first bending wire 25a is loosened. Then, the bending portion 7 is bent in the down direction by total pulling force of the second and third bending wires 25b and 25c. In this case, since rotation operation centered at the central axis O of the lever shaft 40 is restricted by the restriction member 38, a bending operation (inclination operation) by the user is accurately transferred to the wire fixation member 36.

Figure 21:
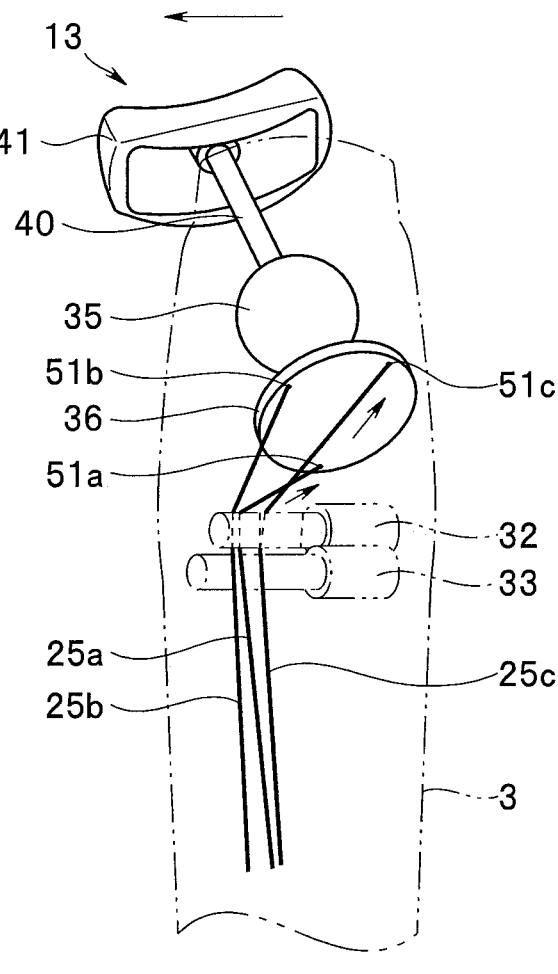
FIG. 21 relates to the embodiment of the present disclosure and is a front view illustrating the state of the bending operation unit and the respective wires when the bending operation lever is inclined in the rightward bending direction.
Figure 22:
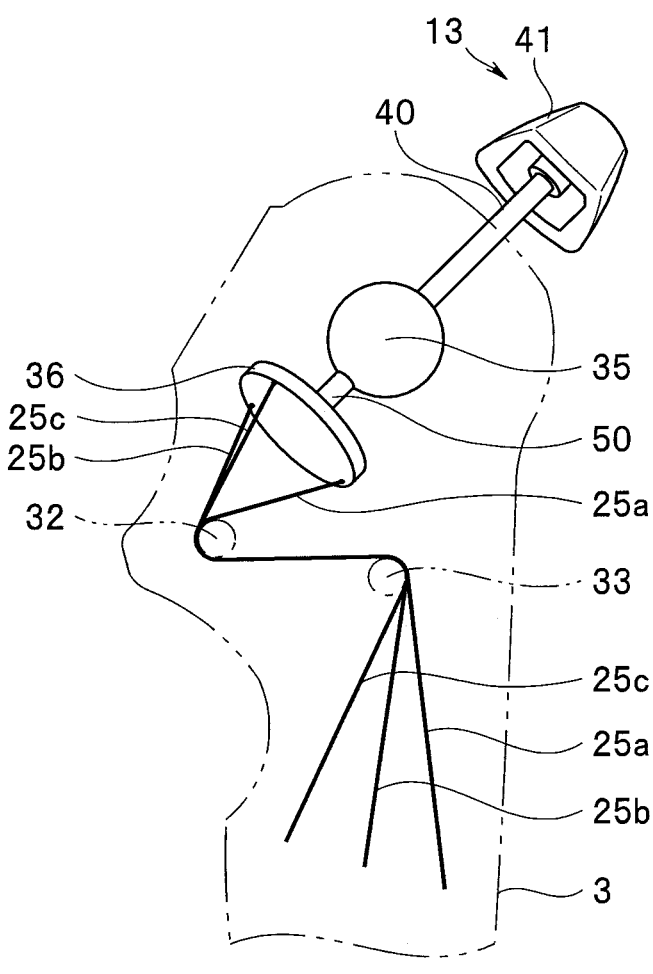
FIG. 22 relates to the embodiment of the present disclosure and is a left side view illustrating the state of the bending operation unit and the respective wires when the bending operation lever is inclined in the rightward bending direction.

As illustrated in, for example, FIGS. 21 and 22, when the bending operation lever 13 is inclined in the right direction, the first and third bending wires 25a and 25c are pulled and the second bending wires 25b is loosened. Then, the bending portion 7 is bent in the right direction by total pulling force of the first and third bending wires 25a and 25c. In this case, since rotation operation centered at the central axis O of the lever shaft 40 is restricted by the restriction member 38, a bending operation (inclination operation) by the user is accurately transferred to the wire fixation member 36.

Figure 23:
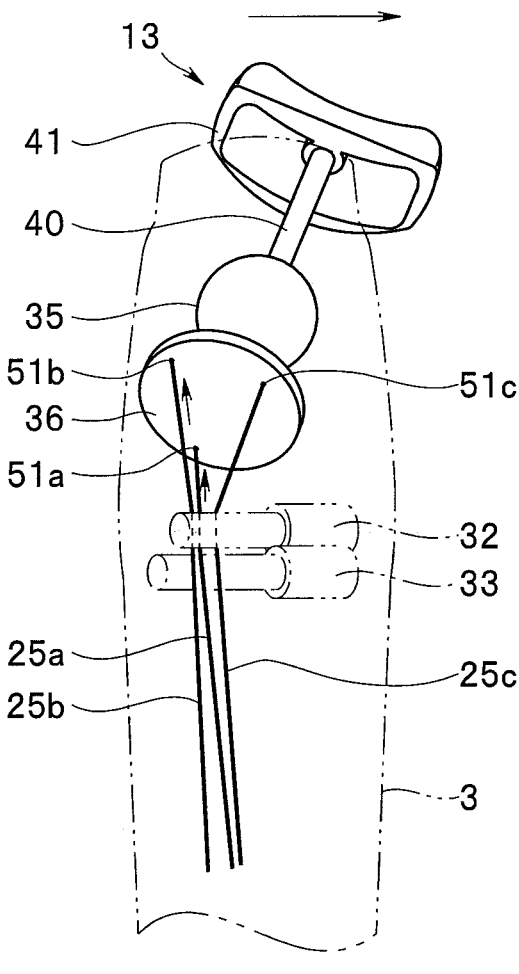
FIG. 23 relates to the embodiment of the present disclosure and is a front view illustrating the state of the bending operation unit and the respective wires when the bending operation lever is inclined in the leftward bending direction.
Figure 24:
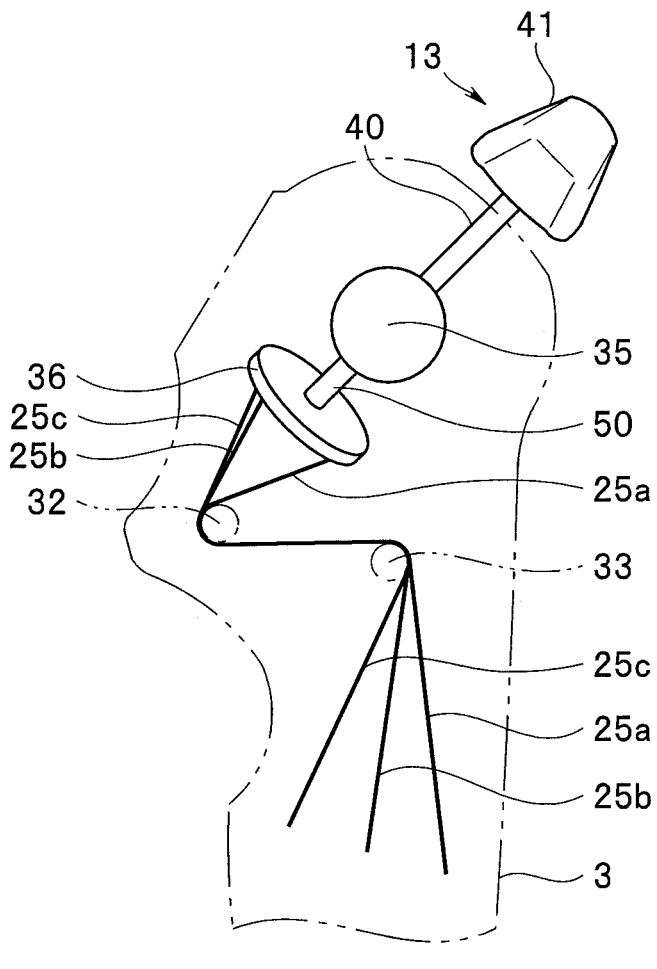
FIG. 24 relates to the embodiment of the present disclosure and is a left side view illustrating the state of the bending operation unit and the respective wires when the bending operation lever is inclined in the leftward bending direction.

As illustrated in, for example, FIGS. 23 and 24, when the bending operation lever 13 is inclined in the left direction, the first and second bending wires 25a and 25b are pulled and the third bending wires 25c is loosened. Then, the bending portion 7 is bent in the left direction by total pulling force of the first and second bending wires 25a and 25b. In this case, since rotation operation centered at the central axis O of the lever shaft 40 is restricted by the restriction member 38, a bending operation (inclination operation) by the user is accurately transferred to the wire fixation member 36.

As described above, the endoscope 1 of the present embodiment includes, in the operation portion 3: the bending operation lever 13; the rotor 35 that rotates in cooperation with motion of the lever shaft 40 of the bending operation lever 13; the wire fixation member 36 that is coupled to the rotor 35 and pulls the first to third bending wires 25a to 25c in cooperation with inclination of the bending operation lever 13; the first and second support members 55 and 56 including the first and second spherical surface portions 57 and 58 that at least part of the rotor 35 internally contacts in a slidable manner by surface contact and rotatably supporting the rotor 35; and the restriction member 38 that is disposed to be able to contact the rotor 35 supported by the first and second support members 55 and 56 and restricts rotation operation centered at the central axis O of the lever shaft 40 of the bending operation lever 13.

Accordingly, with a simple configuration, it is possible to prevent rotation of the bending operation lever 13 about the shaft and achieve an accurate bending operation.

More specifically, the rotor 35 has the concave surface 45 at an outer surface, and the restriction member 38 protrudes inside the concave surface 45 toward the center of the rotor 35. Accordingly, it is possible to allow inclination operation of the bending operation lever 13 in all directions including the up-down direction and the right-left direction but restrict rotation operation of the bending operation lever 13 about the central axis O.

In this case, the concave surface 45 has a V shape formed by the first plane part 45a and the second plane part 45b. The restriction member 38 is made of a plate material (thin plate member) having a tapered shape toward the center of the rotor 35. Accordingly, it is possible to accurately allow inclination operation of the bending operation lever 13 in all directions including the up-down direction and the right-left direction but accurately restrict rotation operation of the bending operation lever 13 about the central axis O.

Since the side surface of the restriction member 38 that contacts the concave surface 45 is formed in a curved shape, it is possible to more accurately allow inclination operation of the bending operation lever 13.

Accordingly, the bending operation mechanism 30 can incline the bending operation lever 13 in the up-down direction, the right-left direction, and a direction as a combination of the up-down direction and the right-left direction (direction as a two-dimensional combination of the up, down, right, and left directions). The bending operation mechanism 30 can pull or loosen the three bending wires 25 (first to third bending wires 25a to 25c) as appropriate in accordance with the inclination state of the bending operation lever 13. Thus, the endoscope 1 of the present embodiment can accurately restrict rotation operation of the bending operation lever 13 about the central axis O while bending the bending portion 7 in all directions.

First Modification

Figure 25:
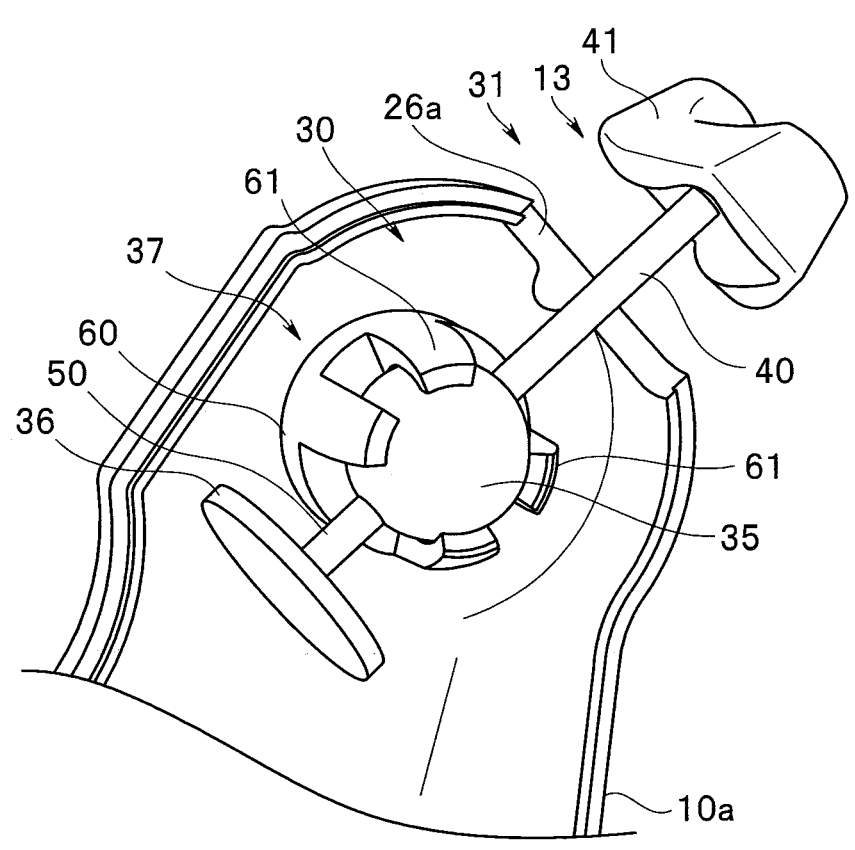
FIG. 25 relates to a first modification and is a perspective view illustrating a main part of the first outer shell and the bending operation mechanism.
Figure 26:
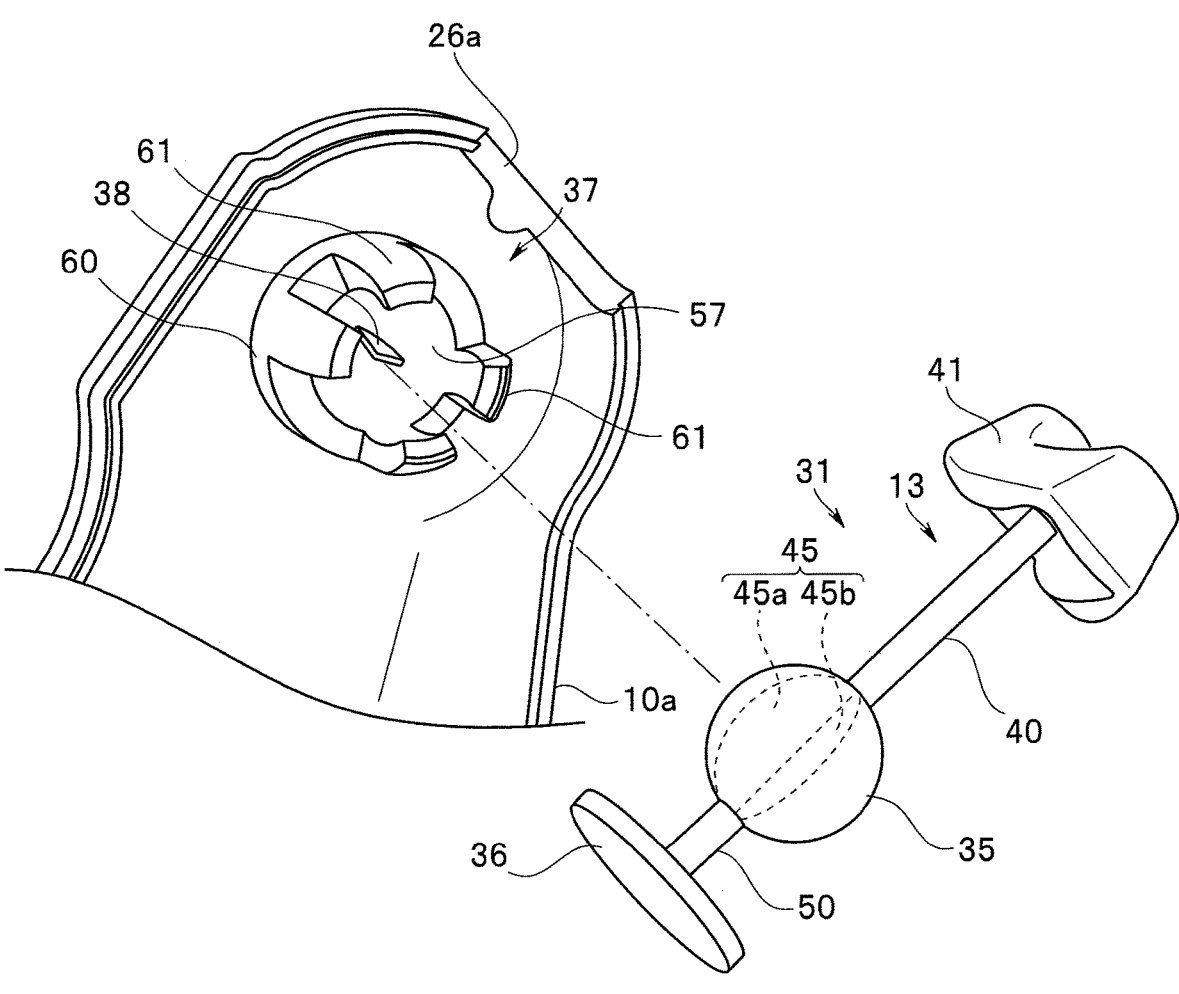
FIG. 26 relates to the first modification and is an exploded perspective view illustrating a main part of the first outer shell and the bending operation mechanism.

Subsequently, a first modification of the above-described embodiment will be described. In the above-described embodiment, the support member 37 employs a configuration in which the rotor 35 is held between the first and second support members 55 and 56 provided at the first outer shell 10a and the second outer shell 10b, respectively. However, as illustrated in, for example, FIGS. 25 and 26, the present modification will be described below for a configuration in which the support member 37 supports the rotor 35 only on the first outer shell 10a side.

In the present modification, the support member 37 includes a base portion 60 protruding from the first outer shell 10a, and a plurality (for example, four) of lock lugs 61 protruding from the base portion 60. Note that the lock lugs 61 are not limited to a configuration in which the lock lugs 61 are integrally formed with the first outer shell 10a (or the second outer shell 10b). For example, the lock lugs 61 may be formed by attaching separate members to the first outer shell 10a (or the second outer shell 10b). The receiver body 37 may include a plurality of lock lugs 61, and the lock lugs 61 support an outer peripheral surface of the rotor 35. The receiver body 37 supports the outer peripheral surface of the rotor 35.

A continuous spherical surface portion 57 is formed at a protrusion end of the base portion 60 and inner surfaces of the respective lock lugs 61. The restriction member 38 is provided inside the spherical surface portion 57 formed at the base portion 60.

The rotor 35 is inserted into the support member 37 with the respective lock lugs 61 elastically deformed. Accordingly, the rotor 35 is rotatably supported by the support member 37 by a snap-fit structure using the respective lock lugs 61.

With such a configuration, it is possible to achieve the same effects as in the above-described embodiment with a simpler configuration.

Second Modification

Figure 27:
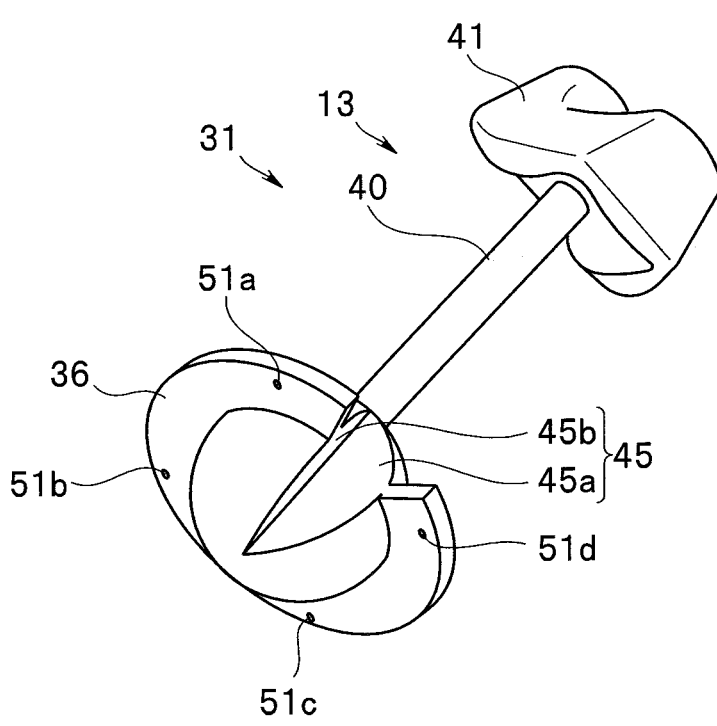
FIG. 27 relates to a second modification and is a perspective view illustrating the bending operation unit.
Figure 28:
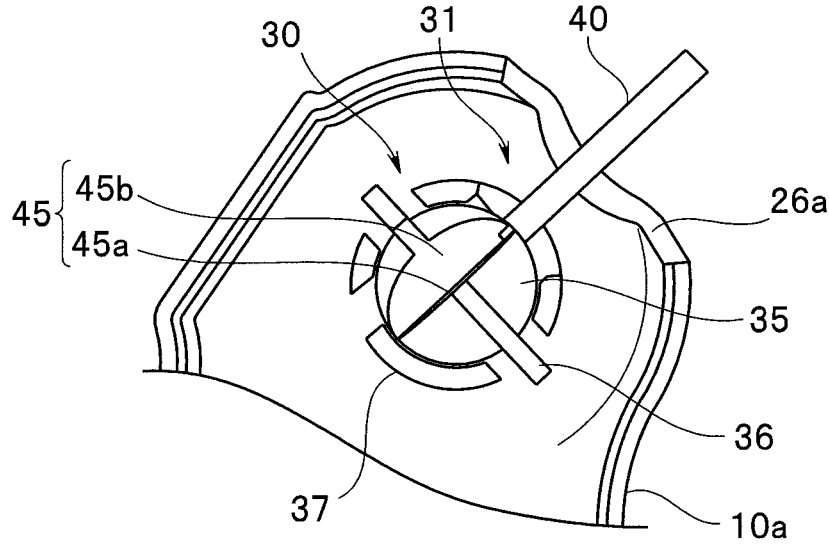
FIG. 28 relates to the second modification and is a perspective view illustrating a main part of the first outer shell and the bending operation mechanism.

Subsequently, a second modification of the above-described embodiment will be described. In the above-described embodiment, the wire fixation member 36 is disposed at a position different from the rotor 35 on the extended line of the central axis O of the bending operation lever 13. However, as illustrated in, for example, FIGS. 27 and 28, the wire fixation member 36 in the bending operation unit 31 of the present modification is disposed at the same position as the rotor 35 on the extended line of the central axis O of the bending operation lever 13.

Note that, in the present modification, first to fourth wire fixation portions 51a to 51d are provided at four positions that are rotationally symmetric with respect to the central point P of the rotor 35. A fourth wire is provided inside the insertion portion 2 and attached to the wire attachment surface 51d. The wire attachment surface 51d is provided on the outer peripheral surface of the rotor 35, and each of the first bending wire 25a, the second bending wire 25b, the third bending wire 25c and the fourth bending wire extend from the wire attachment surfaces 51a to 51d to the bending portion 7.

Such a configuration achieves, in addition to the same effects as in the above-described embodiment, an effect that an inclination operation of the bending operation lever 13 can be more accurately transferred to the bending portion 7 because the wire fixation member 36 inclines with respect to the central point P of the rotor 35.

Third Modification

Figure 29:
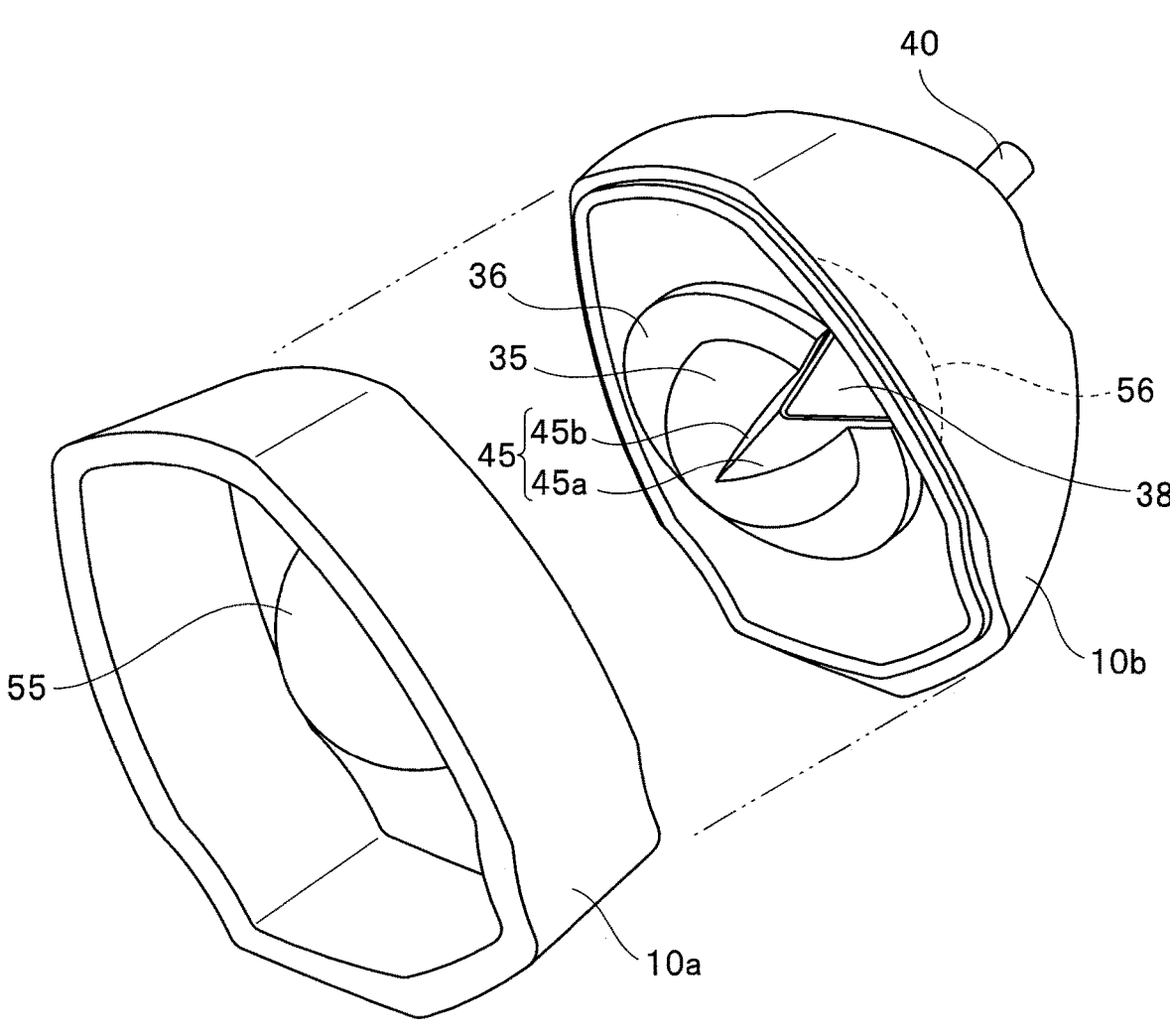
FIG. 29 relates to a third modification and is a perspective view illustrating a main part of the bending operation mechanism from which the second outer shell is removed.

Subsequently, a third modification of the above-described embodiment will be described. In the present modification, as illustrated in, for example, FIG. 29, the outer shell constituting the operation portion 3 is divided into the first outer shell 10a constituting the distal end side of the operation portion 3, and the second outer shell 10b constituting the proximal end side of the operation portion 3.

In this case, the support member 37 includes, for example, the first support member 55 provided at the first outer shell 10a, and the second support member 56 provided at the second outer shell 10b.

The restriction member 38 is provided at, for example, the second support member 56.

In such a modification, for example, the rotor 35 of the bending operation unit 31 described above in the second modification can be supported by being held between the distal end side and the proximal end side.

Fourth Modification

Figure 30:
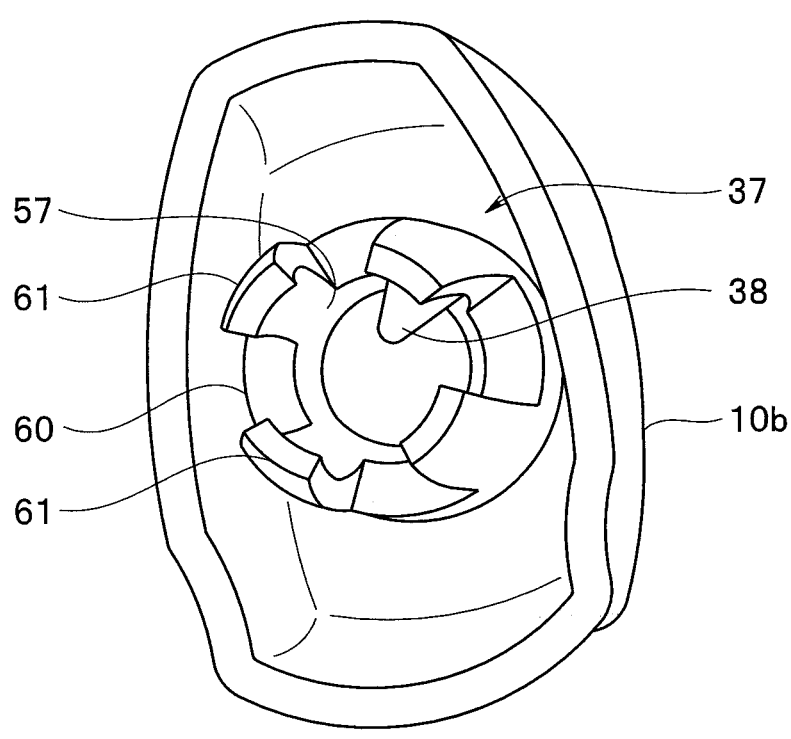
FIG. 30 relates to a fourth modification and is a perspective view illustrating the first outer shell.
Figure 31:
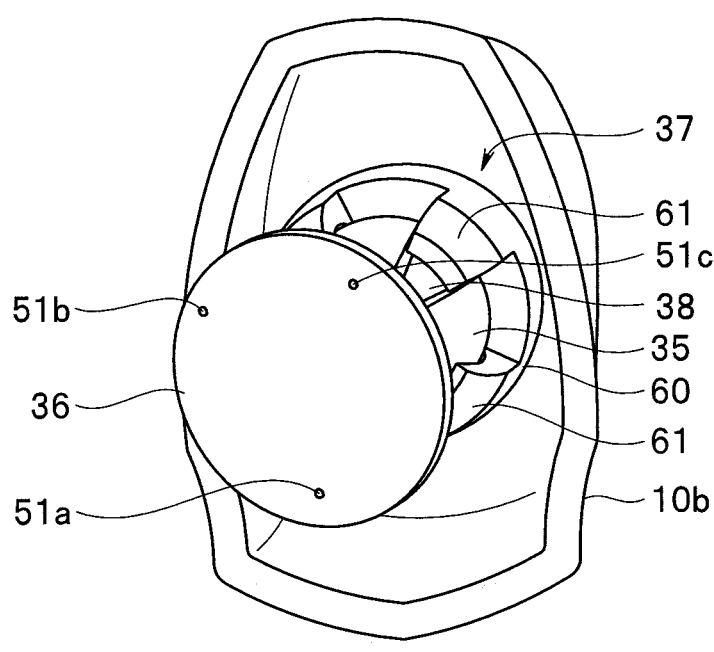
FIG. 31 relates to the fourth modification and is a perspective view illustrating a main part of the first outer shell and the bending operation mechanism.

Subsequently, a fourth modification of the above-described embodiment will be described. In the present modification, as illustrated in, for example, FIGS. 30 and 31, the support member 37 described above in the second modification is applied to the second outer shell 10b described above in the third modification.

Moreover, for example, the rotor 35 of the bending operation unit 31 described above in the embodiment is rotatably supported by the support member 37.

Fifth Modification

Figure 32:
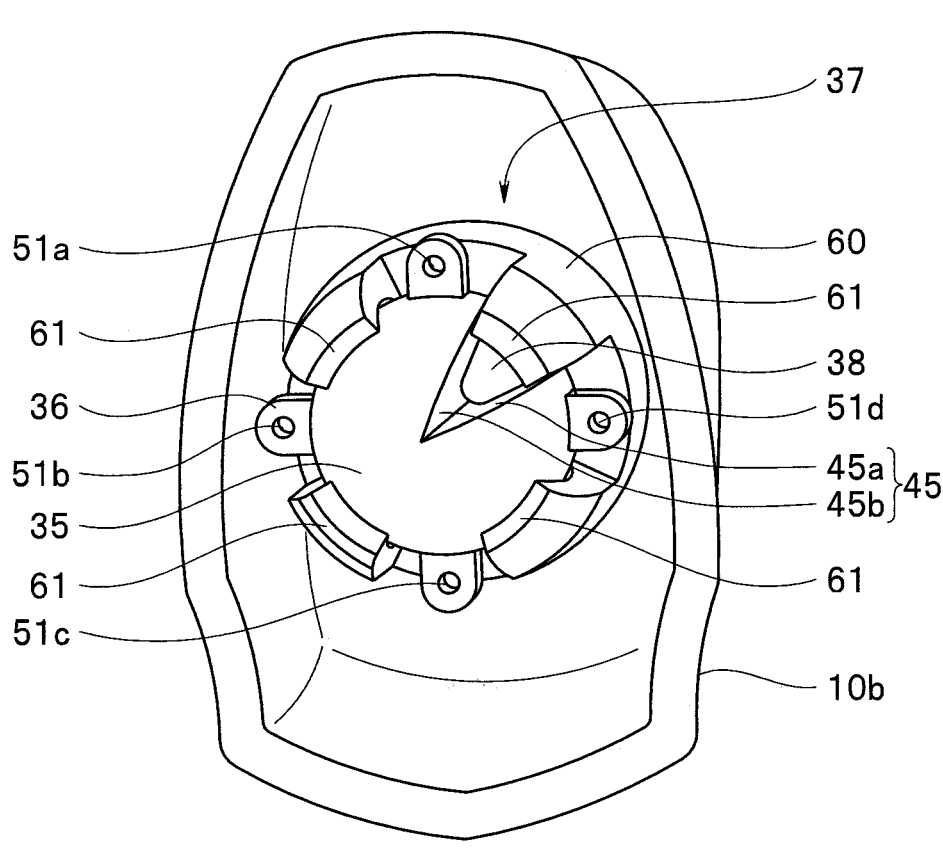
FIG. 32 relates to a fifth modification and is a perspective view illustrating a main part of the first outer shell and the bending operation mechanism.

Subsequently, a fifth modification of the above-described embodiment will be described. In the present modification, as illustrated in, for example, FIG. 32, the support member 37 described above in the second modification is applied to the second outer shell 10b described above in the third modification.

In the present modification, for example, the rotor 35 of the bending operation unit 31 described above in the second modification is supported by the support member 37. However, in the wire fixation member 36, notches for preventing interference with the respective lock lugs 61 are provided at the positions corresponding to the respective lock lugs 61. And the first to fourth wire fixation portions 51a to 51d may be individually provided between each of the respective lock lugs 61.

Sixth Modification

Figure 33:
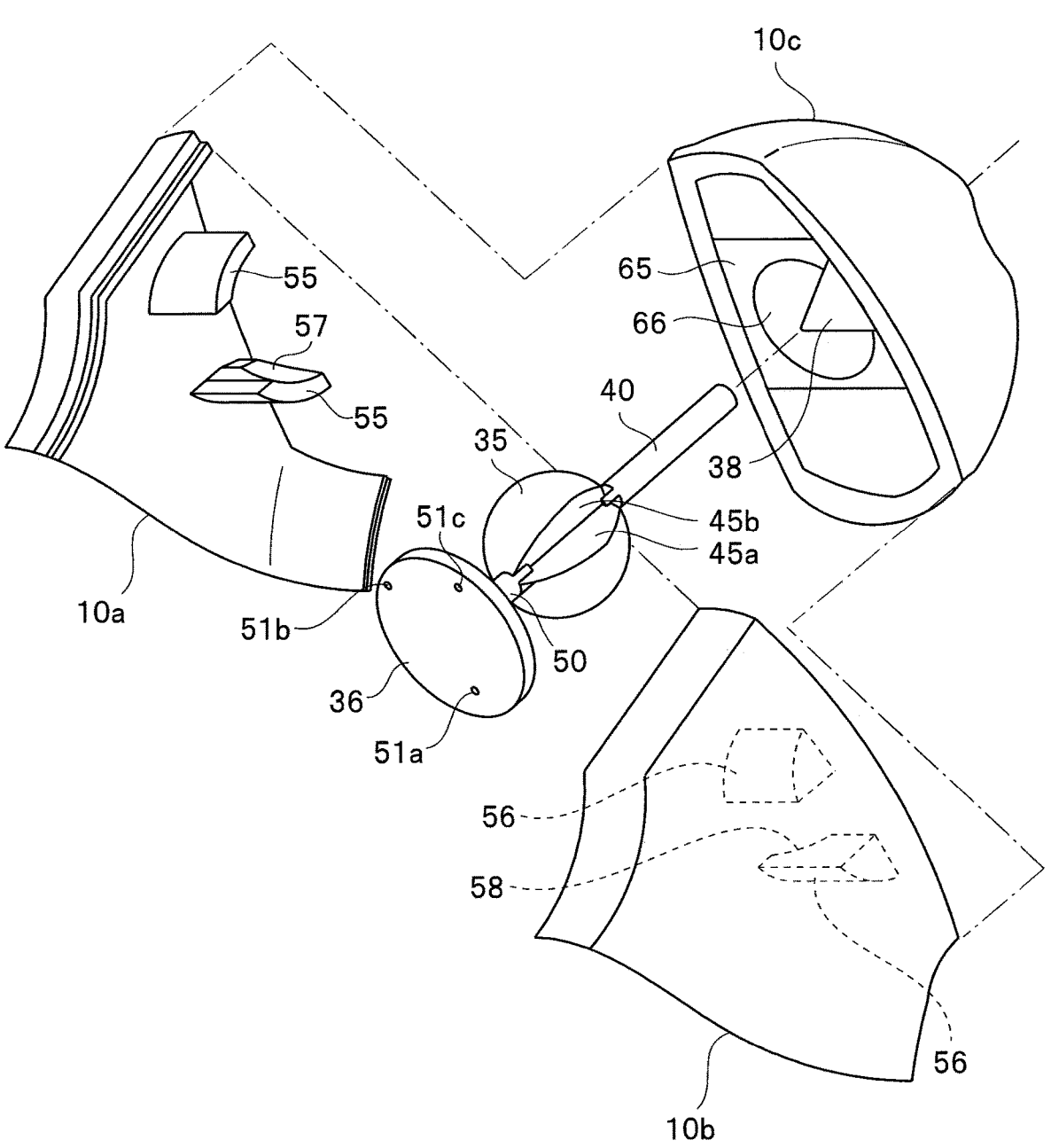
FIG. 33 relates to a sixth modification and is a perspective view illustrating a main part of first to third outer shells and the bending operation mechanism.

Subsequently, a sixth modification of the above-described embodiment will be described. The present modification will be described below for a configuration in which the outer shell constituting the operation portion 3 is divided into three as illustrated in, for example, FIG. 33.

In the present modification, the outer shell 10 constituting the operation portion 3 includes the first and second outer shells 10a and 10b into which the distal end side of the operation portion 3 is divided in the right-left direction, and a third outer shell 10c coupled to proximal ends of the first and second outer shells 10a and 10b.

The column-shaped first and second support members 55 and 56 are provided at the inner surfaces of the first and second outer shells 10a and 10b. The first and second spherical surface portions 57 and 58 are formed at the first and second support members 55 and 56.

In addition, a third support member 65 having a thick plate shape is provided at an inner surface of the third outer shell 10c. A third spherical surface portion 66 is formed at the third support member 65.

The first to third spherical surface portions 57, 58, and 66 are set so that central points of which match when the first to third outer shells 10a to 10c are bonded to one another.

When the outer shell 10 is assembled, first, the first outer shell 10a and the second outer shell 10b are bonded to each other. In this case, the rotor 35 is held between the first spherical surface portion 57 and the second spherical surface portion 58. Thereafter, the third outer shell 10c is bonded to the proximal ends of the coupled first and second outer shells 10a and 10b. Accordingly, the rotor 35 is rotatably supported by the first to third support members 57, 58, and 66.

Seventh Modification

Figure 34:
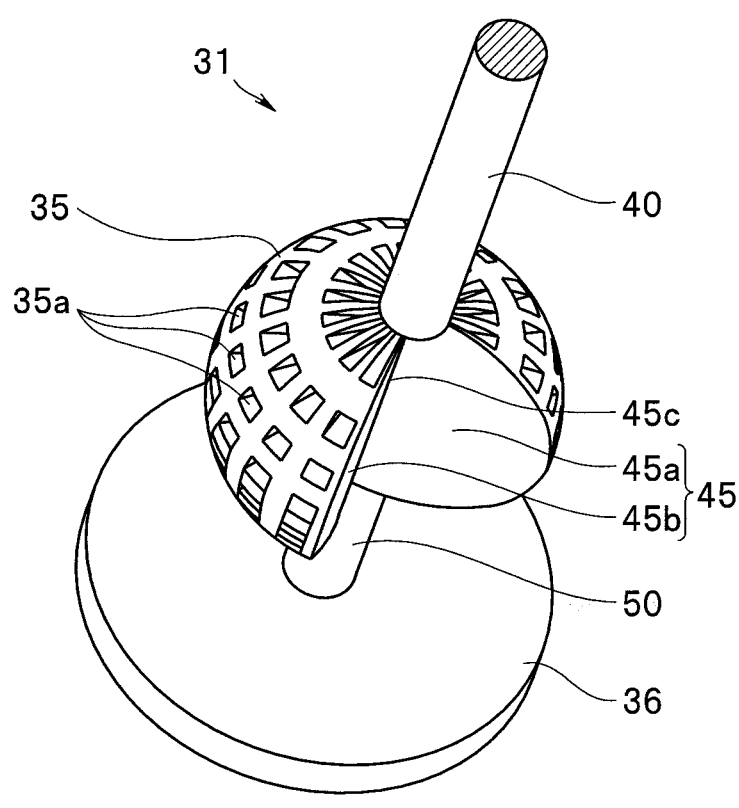
FIG. 34 relates to a seventh modification and is a perspective view illustrating a main part of the bending operation unit.

Subsequently, a seventh modification of the above-described embodiment will be described. The present modification will be described below for a configuration for weight reduction of the rotor 35 as illustrated in, for example, FIG. 34.

Thus, in the present modification, a plurality of lightening holes 35a are formed through the rotor 35. Note that the rotor 35 may be formed as a sphere having a spoke shape.

Eighth Modification

Figure 35:
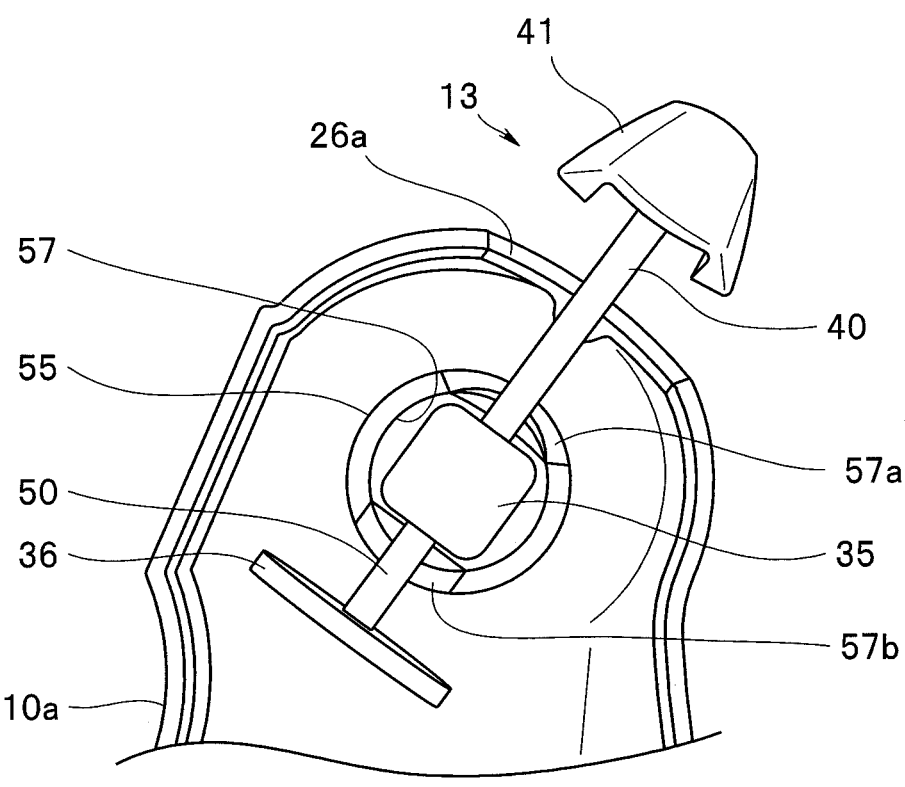
FIG. 35 relates to an eighth modification and is a perspective view illustrating a main part of the bending operation mechanism from which the second outer shell is removed.

Subsequently, an eighth modification of the above-described embodiment will be described. In the present modification, the rotor 35 is formed as a polyhedron as illustrated in, for example, FIGS. 35 and 36.

Figure 36:
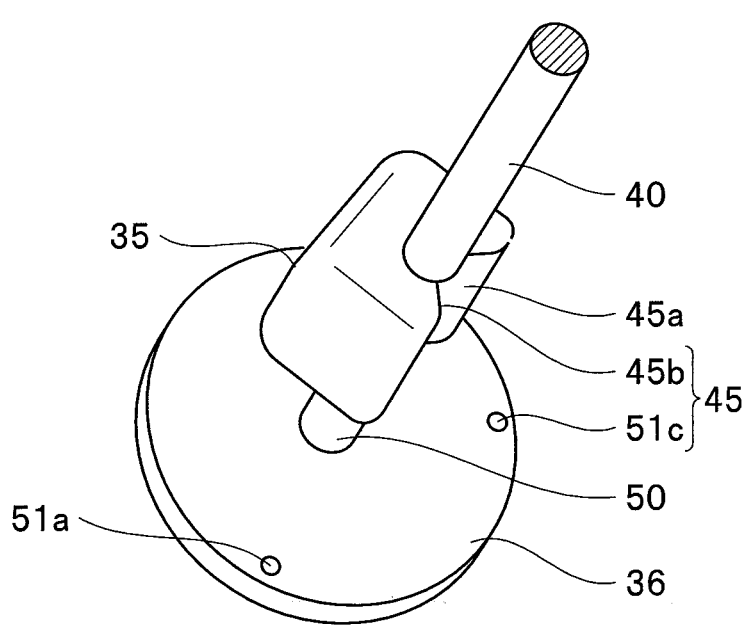
FIG. 36 relates to the eighth modification and is a perspective view illustrating a main part of the bending operation unit.

In the present modification, the rotor 35 is formed as, for example, a hexahedron as illustrated in, for example, FIG. 36. Note that the rotor 35 may be formed as a polyhedron higher than a hexahedron.

The rotor 35 thus configured internally contacts the first and second spherical surface portions 57 and 58 in a slidable manner by point contact.

Ninth Modification

Figure 37:
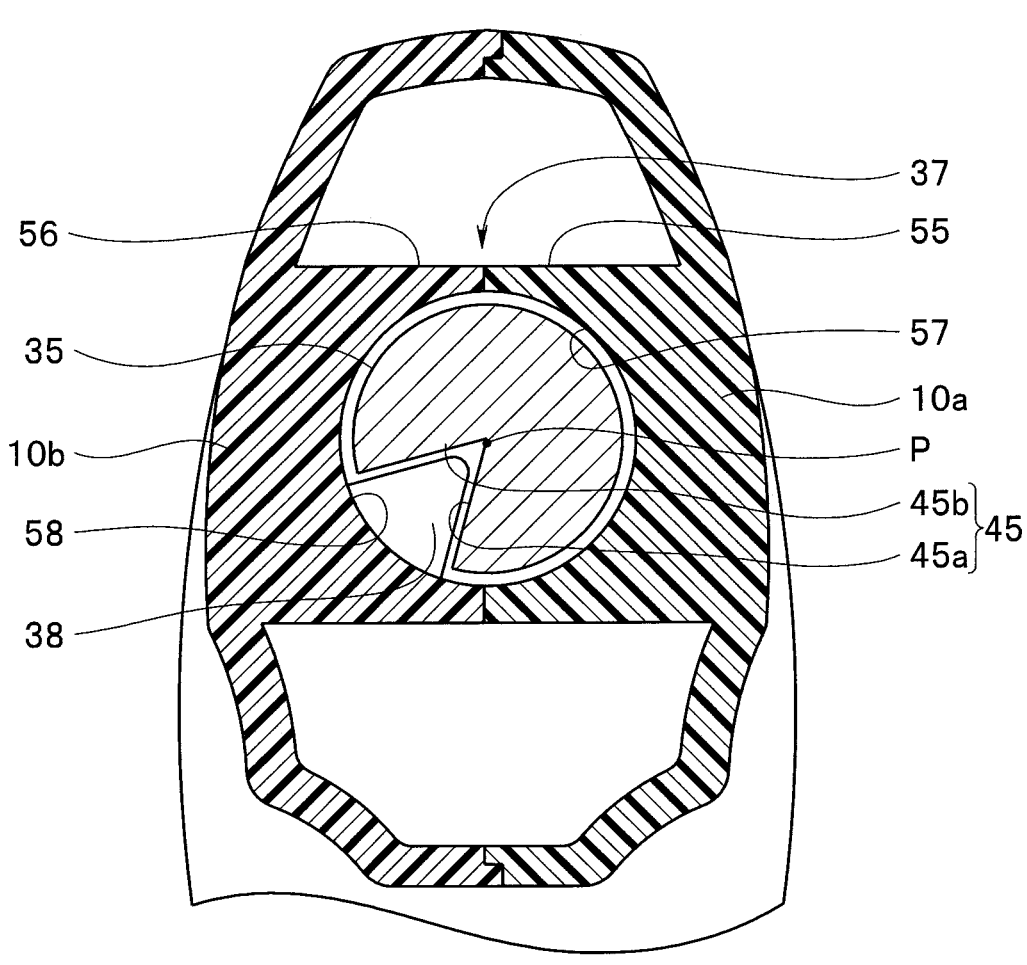
FIG. 37 relates to a ninth modification and is a main-part cross-sectional view of an operation portion.

Subsequently, a ninth modification of the above-described embodiment will be described. In the present modification, as illustrated in, for example, FIG. 37, the angle between the first plane part 45a and the second plane part 45b forming the concave surface 45 is set to be smaller than 90°. Note that, along with such angle change, an angle of the restriction member 38 is changed as well.

Tenth Modification

Figure 38:
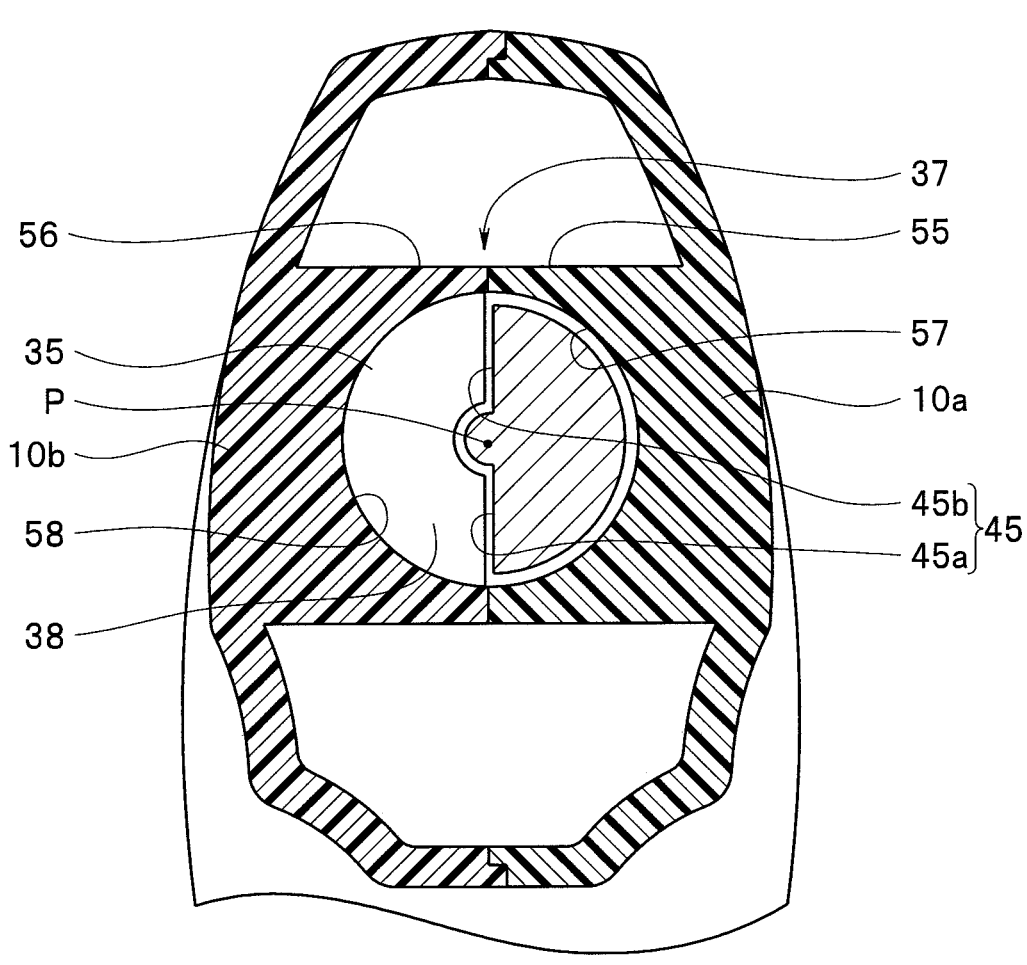
FIG. 38 relates to a tenth modification and is a main-part cross-sectional view of the operation portion.

Subsequently, a tenth modification of the above-described embodiment will be described. In the present modification, as illustrated in, for example, FIG. 38, the angle of the first plane part 45a and the second plane part 45b forming the concave surface 45 is set to be larger than 90°. The angle between the first plane part 45a and the second plane part 45b in the present modification is 180°, for example. Note that, along with such angle change, the angle of the restriction member 38 is changed as well.

Eleventh Modification

Figure 39:
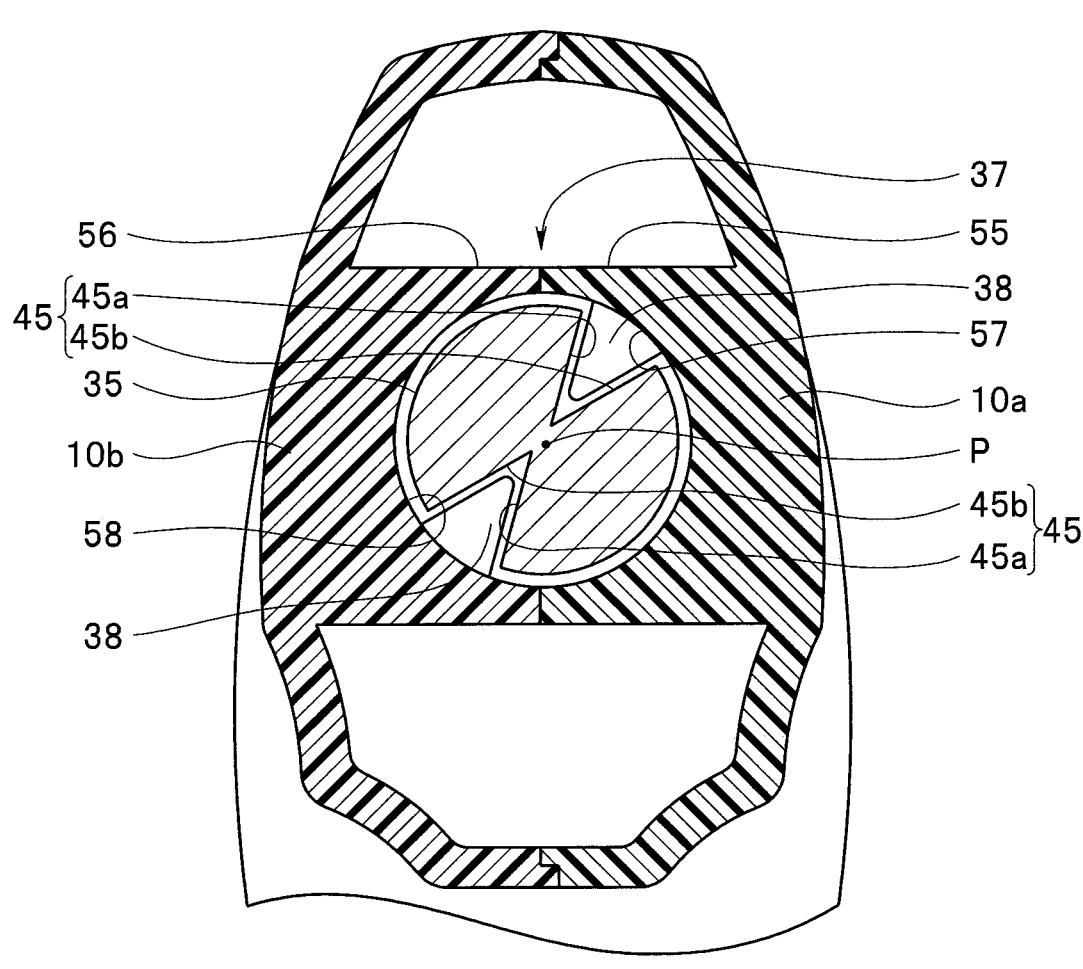
FIG. 39 relates to an eleventh modification and is a main-part cross-sectional view of the operation portion.

Subsequently, an eleventh modification of the above-described embodiment will be described. In the present modification, the rotor 35 has a pair of concave surfaces 45 as illustrated in, for example, FIG. 39. Accordingly, the restriction member 38 is provided at each of the first spherical surface portion 57 and the second spherical surface portion 58.

Twelfth Modification

Figure 40:
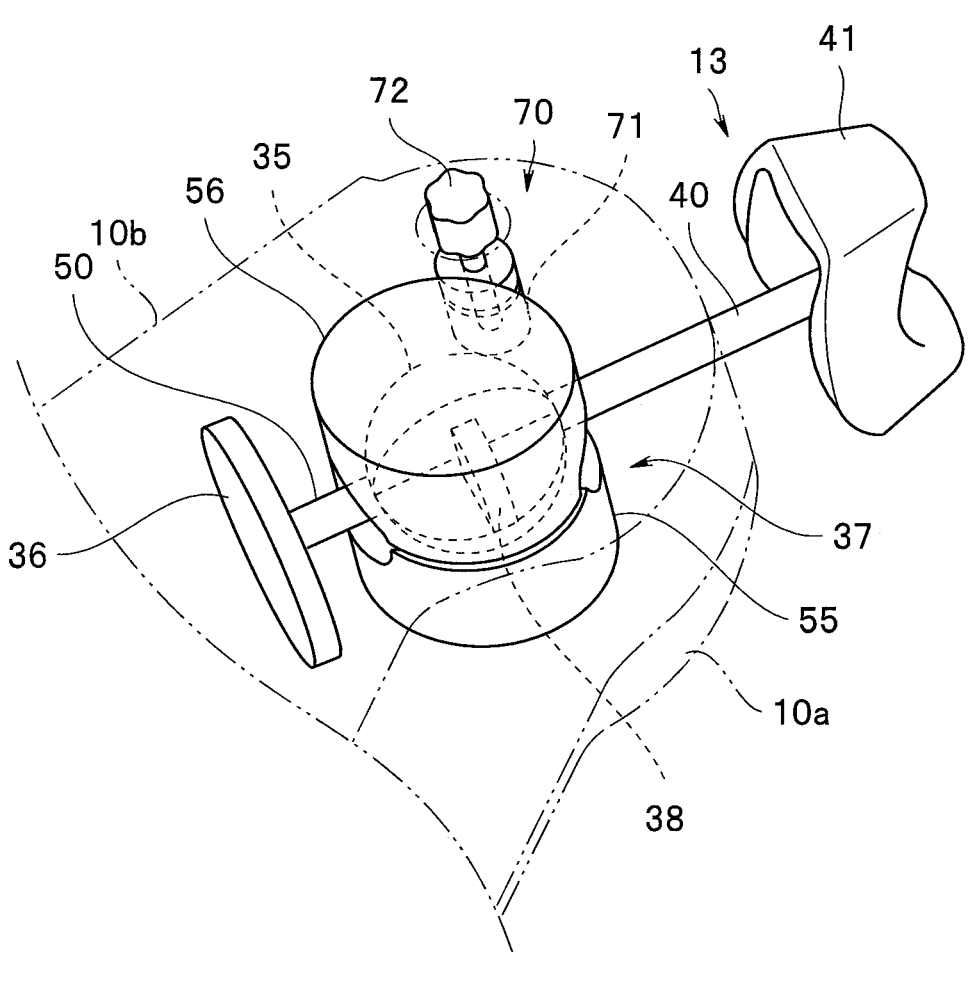
FIG. 40 relates to a twelfth modification and is a perspective view illustrating a main part of the bending operation mechanism and a braking member.

Subsequently, a twelfth modification of the above-described embodiment will be described. The present modification will be described below for a configuration in which a lock mechanism 70 (or pressure adjustment mechanism) is added to the operation portion 3 as illustrated in, for example, FIG. 40.

The lock mechanism 70 fixes operation of the rotor 35 at a predetermined rotational position by adding friction to the rotor 35 through an operation of the operation portion 3 from outside.

To achieve such fixation of the rotor 35, the lock mechanism 70 includes, for example, a boss 71 provided near the first support member 55 on the inner surface of the first outer shell 10a, and an adjustment screw 72 that is screwed into the boss 71 from outside of the second outer shell 10b.

In the lock mechanism 70 of the present modification, the first and second outer shells 10a and 10b elastically deform inward by increasing an amount of screwing of the adjustment screw 72 into the boss 71. The bending operation unit includes the pressure adjustment mechanism 70 having a pressing surface, and the pressure adjustment mechanism 70 is configured to adjust a friction contact between the pressing surface and the receiver body 37. The pressure adjustment mechanism 70 may be configured to indirectly adjust a friction contact between and the receiver body 37 and one or more of the first spherical surface portion 57 and the second spherical surface portion 58. The friction contact is sufficient to prevent the rotation of the rotor 35.

Accordingly, the first spherical surface portion 57 of the first support member 55 and the second spherical surface portion 58 of the second support member 56 are pressed against the rotor 35 and fix operation of the rotor 35.

Thirteenth Modification

Figure 41:
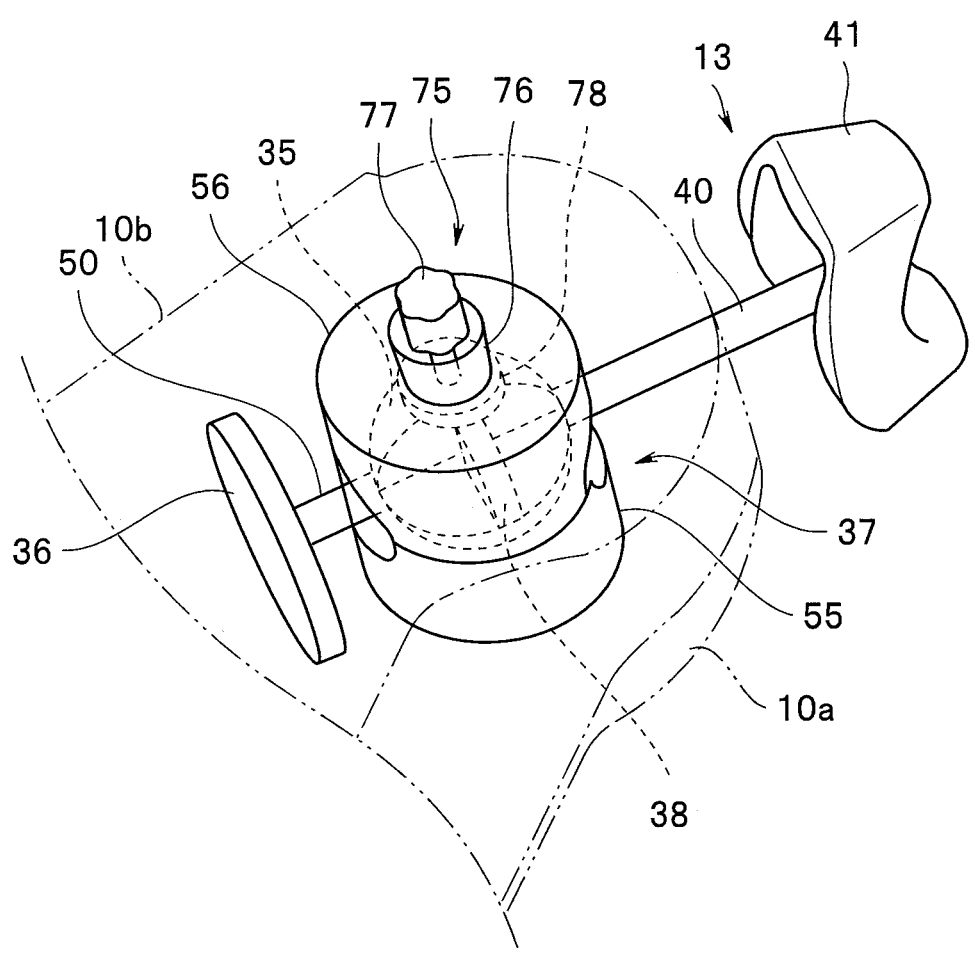
FIG. 41 relates to a thirteenth modification and is a perspective view illustrating a main part of the bending operation mechanism and the braking member.

Subsequently, a thirteenth modification of the above-described embodiment will be described. The present modification will be described below for a configuration in which a lock mechanism 75 (or pressure adjustment mechanism) is added to the operation portion 3 as illustrated in, for example, FIG. 41.

The lock mechanism 75 of the present modification includes a boss 76 provided on the inner surface of the second outer shell 10b, an adjustment screw 76 that is screwed into the boss 76 from outside of the second outer shell 10b, and a brake pad 77 provided at a distal end of the adjustment screw 76.

In the lock mechanism of the present modification, the brake pad 77 is pressed against the rotor 35 inside the second support member 56 by increasing an amount of screwing of the adjustment screw 76 into the boss 76. Accordingly, the lock mechanism 75 fixes operation of the rotor 35. The bending operation unit includes the pressure adjustment mechanism 75 having a pressing surface, and the pressure adjustment mechanism 75 is configured to adjust a friction contact between the pressing surface and the receiver body 37. The pressure adjustment mechanism 75 may be configured to indirectly adjust a friction contact between and the receiver body 37 and one or more of the first spherical surface portion 57 and the second spherical surface portion 58. The friction contact is sufficient to prevent the rotation of the rotor 35.

Fourteenth Modification

Figure 42:
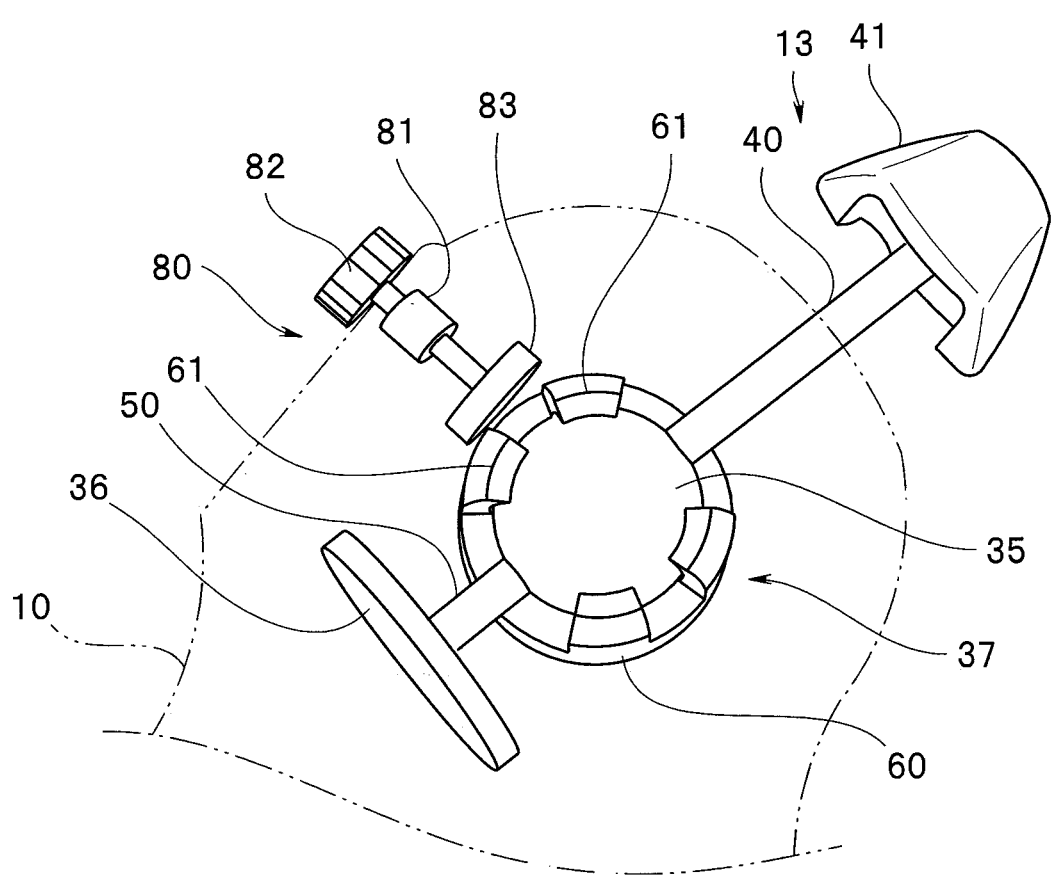
FIG. 42 relates to a fourteenth modification and is a perspective view illustrating a main part of the bending operation mechanism and the braking member.

Subsequently, a fourteenth modification as a modification of the above-described second modification will be described. The present modification will be described below for a configuration in which a lock mechanism 80 is added to the operation portion 3 as illustrated in, for example, FIG. 42.

The lock mechanism 80 of the present modification includes a boss 81 protruding from the inner surface of the second outer shell 10b toward the lock lugs 61 of the support member 37, an adjustment screw 82 that is screwed into the boss 81 from outside of the second outer shell 10b, and a pressing member 83 provided at a distal end of the adjustment screw 82.

In the lock mechanism 80 of the present modification, the pressing member 83 (or pressing surface) is pressed against the lock lugs 61 inside the outer shell 10 by increasing an amount of screwing of the adjustment screw 82 into the boss 81. Accordingly, in the lock mechanism 81, the lock lugs 61 are pressed against the rotor 35 and fix operation of the rotor 35. The bending operation unit includes the pressure adjustment mechanism 80 having the pressing surface 83, and the pressure adjustment mechanism 80 is configured to adjust a friction contact between the pressing surface 83 and the receiver body 37. The pressure adjustment mechanism 80 may be configured to indirectly adjust a friction contact between and the receiver body 37 and one or more of the first spherical surface portion 57 and the second spherical surface portion 58. The friction contact is sufficient to prevent the rotation of the rotor 35.

Fifteenth Modification

Figure 43:
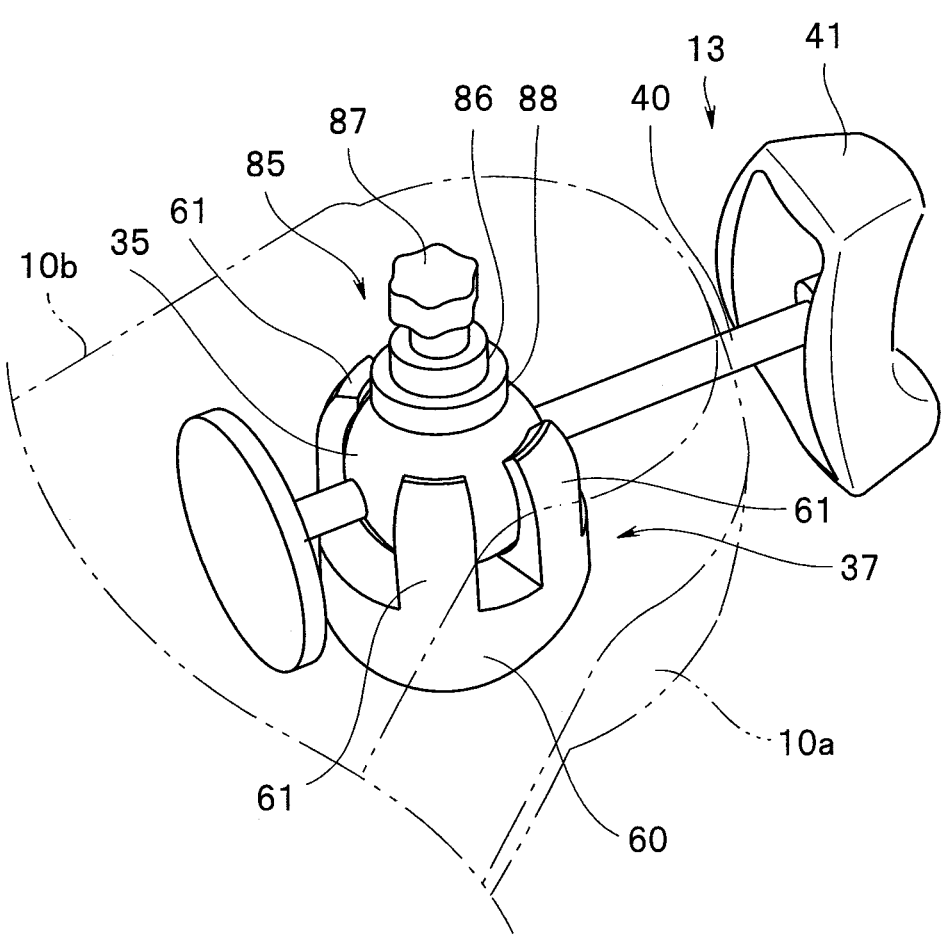
FIG. 43 relates to a fifteenth modification and is a perspective view illustrating a main part of the bending operation unit.

Subsequently, a fifteenth modification as a modification of the above-described second modification will be described below. The present modification will be described below for a configuration in which a lock mechanism 85 is added to the operation portion 3 as illustrated in, for example, FIG. 43.

The lock mechanism 85 of the present modification includes a boss 86 protruding from the inner surface of the second outer shell 10*b* toward the rotor 35, an adjustment screw 87 that is screwed into the boss 86 from outside of the second outer shell 10*b*, and a brake pad 88 provided at a distal end of the adjustment screw 87.

In the lock mechanism 85 of the present modification, the brake pad 88 (or pressing surface) is pressed against the rotor 35 inside the outer shell 10 by increasing an amount of screwing of the adjustment screw 87 into the boss 86. Accordingly, the lock mechanism 85 fixes operation of the rotor 35. The bending operation unit includes the pressure adjustment mechanism 85 having the pressing surface 88, and the pressure adjustment mechanism 85 is configured to adjust a friction contact between the pressing surface 88 and the receiver body 37. The pressure adjustment mechanism 85 may be configured to indirectly adjust a friction contact between and the receiver body 37 and one or more of the first spherical surface portion 57 and the second spherical surface portion 58. The friction contact is sufficient to prevent the rotation of the rotor 35.

Sixteenth Modification

Figure 44:
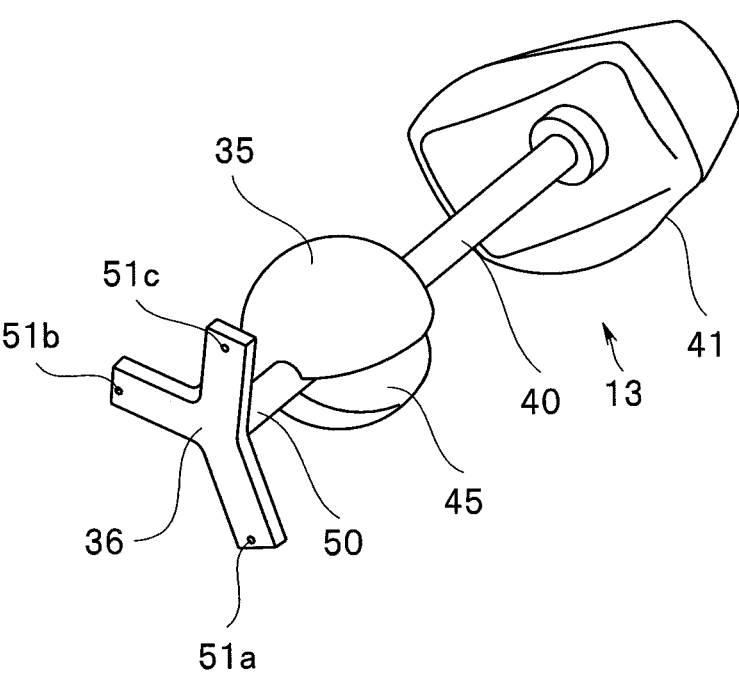
FIG. 44 relates to a sixteenth modification and is a perspective view illustrating a main part of the bending operation unit.

Subsequently, a sixteenth modification of the above-described embodiment will be described. The present modification will be described below for a configuration for simplifying the wire fixation member 36 as illustrated in, for example, FIG. 44.

In the wire fixation member 36 of the present modification, parts other than parts at which the first to third wire fixation portions 51*a* to 51*c* are provided are cut out. Accordingly, the wire fixation member 36 is simplified.

Seventeenth Modification

Figure 45:
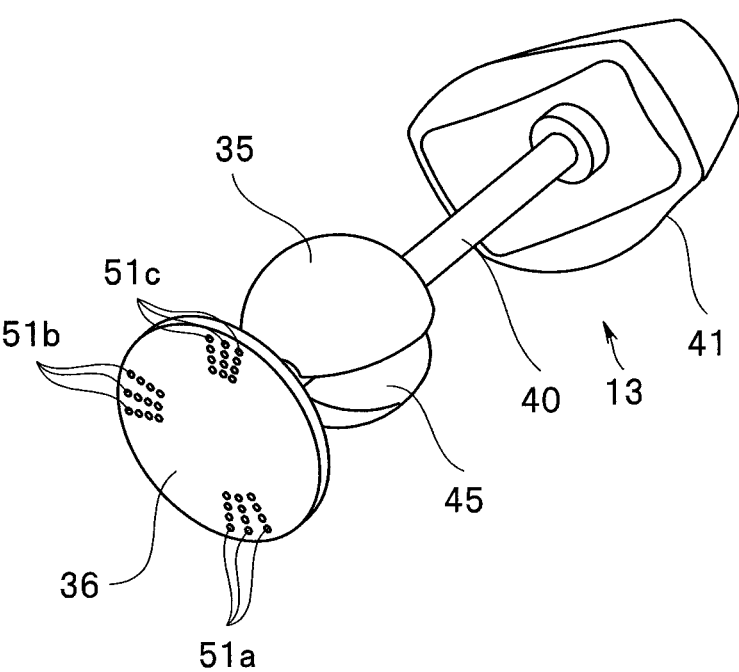
FIG. 45 relates to a seventeenth modification and is a perspective view illustrating a main part of the bending operation unit.

Subsequently, a seventeenth modification of the above-described embodiment will be described. The present modification will be described below for a configuration with variable positions at which the first to third bending wires 25*a* to 25*c* are fixed to the wire fixation member 36 as illustrated in, for example, FIG. 45.

The wire fixation member 36 of the present modification includes a plurality of first wire fixation portions 51*a*, a plurality of second wire fixation portions 51*b*, and a plurality of third wire fixation portions 51*c*. The sets of first to third wire fixation portions 51*a* to 51*c* are each arrayed in a matrix.

The first to third bending wires 25*a* to 25*c* are each selectively fixed to any of the plurality of first to third wire fixation portions 51*a* to 51*c*. Accordingly, positions at which the first to third bending wires 25*a* to 25*c* are attached to the wire fixation member 36 can be variably set.

Eighteenth Modification

Figure 46:
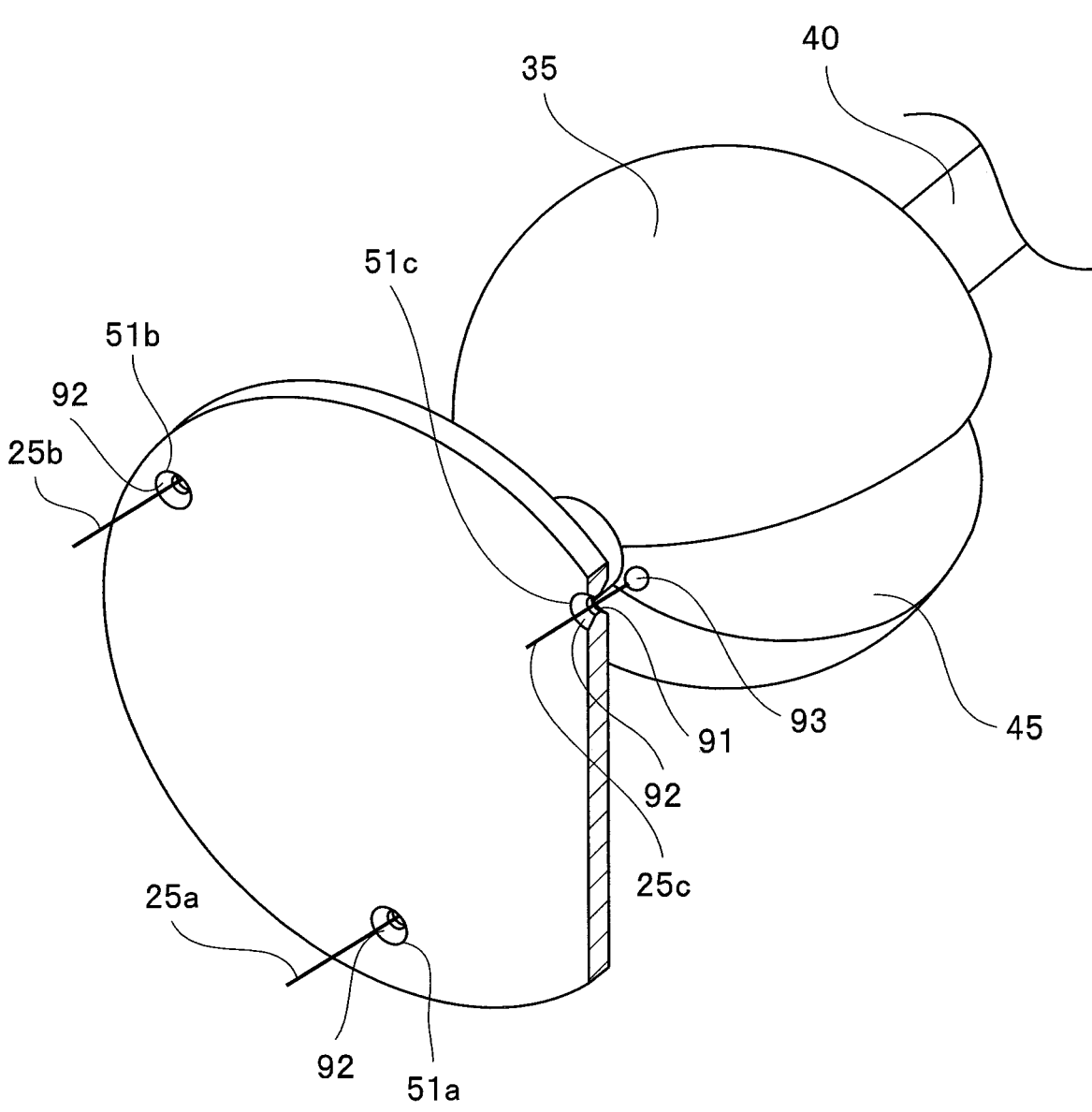
FIG. 46 relates to an eighteenth modification and is a perspective view illustrating a main part of the bending operation unit.

Subsequently, an eighteenth modification of the above-described embodiment will be described. The present modification will be described below for a configuration for fixing the first to third bending wires 25*a* to 25*c* to the wire fixation member 36 in an inclinable manner as illustrated in, for example, FIG. 46.

The first to third wire fixation portions 51*a* to 51*c* of the present modification each have a first tapering surface 91 having a diameter that decreases from one surface of the wire fixation member 36 toward inside in a thickness direction of the wire fixation member 36, and a second tapering surface 92 having a diameter that decreases from the other surface of the wire fixation member 36 toward inside in the thickness direction of the wire fixation member 36. The tapering surface 91 forms a first tapered hole. The second tapering surface 92 forms a second tapered hole.

In addition, a lock member 93 having a spherical shape is fixed at a proximal end of each of the first to third bending wires 25*a* to 25*c* of the present modification.

The respective lock members 93 are locked to the first to third wire fixation portions 51*a* to 51*c* from the first tapering surface 91 side.

Accordingly, the respective lock members 93 are rotatably locked to the first tapering surface 91. Moreover, the first to third bending wires 25*a* to 25*c* can be inclined in an angle range of tilt of the second tapering surface 92 without bending by a surface of the wire fixation member 36. The wire attachment surface includes one or more of the first tapered hole 91 and the second tapered hole 92 to which the first bending wire 25*a* is attached.

Nineteenth Modification

Figure 47:
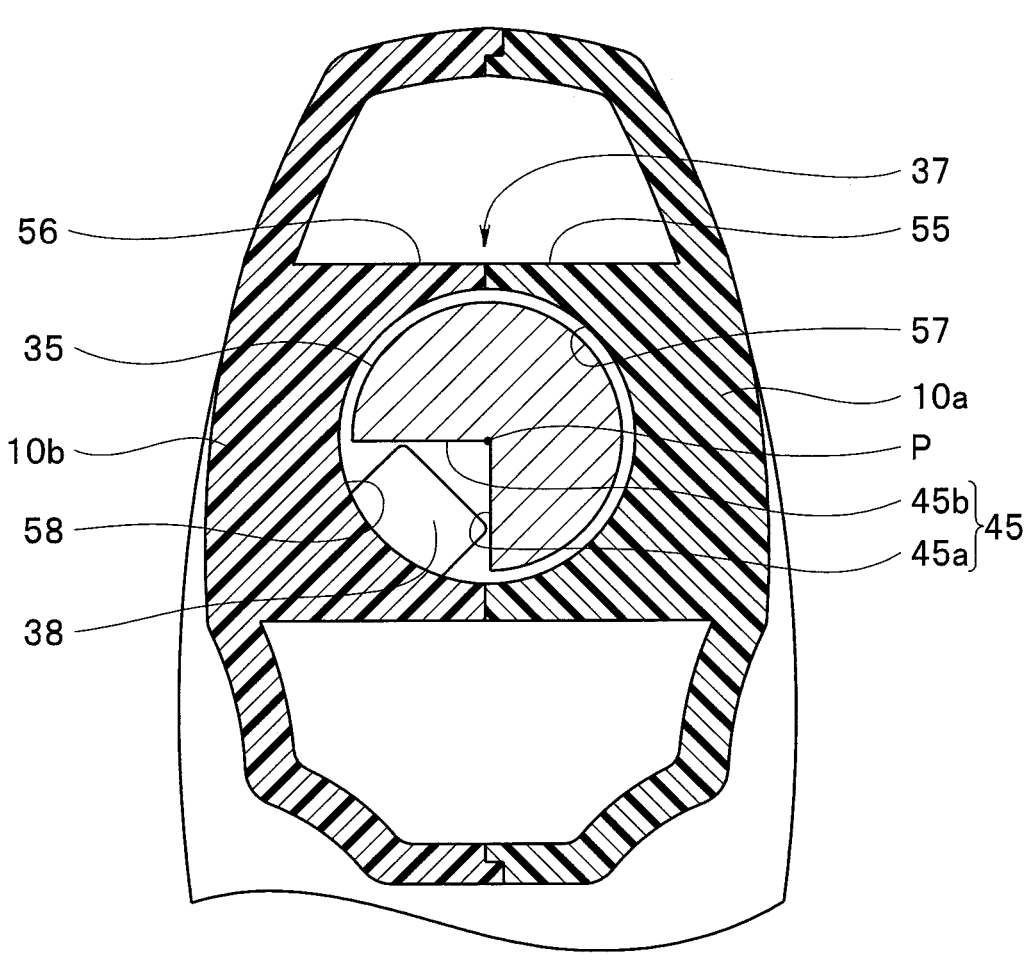
FIG. 47 relates to a nineteenth modification and is a main-part cross-sectional view of the operation portion.

Subsequently, a nineteenth modification of the above-described embodiment will be described. In the present modification, the restriction member 38 has a shape different from the shape in the above-described embodiment. In other words, the restriction member 38 of the present modification is formed in a substantially rectangular shape in a plan view as illustrated in, for example, FIG. 47. A shape of the restriction member 38 that performs same function or movement as this disclosure is defined in the substantially triangular shape.

In the restriction member 38 of the present modification, two corners protruding inside the concave surface 45 point-contact the first plane part 45*a* and the second plane part 45*b*, respectively. Accordingly, the restriction member 38 restricts rotation operation centered at the central axis O of the lever shaft 40 of the bending operation lever 13 but allows inclination operation of the bending operation lever 13 in any direction.

Note that the present disclosure is not limited to the above-described embodiment and respective modifications but may be provided with various kinds of modifications and changes, which are in the technical scope of the present disclosure. For example, components of the above-described embodiment and respective modifications may be combined as appropriate.

Example 1. An insertion instrument comprising:

an operation portion;

a bending portion provided at an insertion portion continuously provided with the operation portion;

a lever that includes a shaft extending from inside of the operation portion toward outside of the operation portion and inclines upon reception of operation force from outside of the operation portion;

a rotor that rotates in cooperation with motion of the shaft inside the operation portion;

a wire fixation member that is coupled to the rotor inside the operation portion and pulls at least one wire that bends the bending portion in cooperation with inclination of the lever;

a support member including a spherical surface portion that at least part of the rotor internally contacts in a slidable manner by surface contact or point contact and rotatably supporting the rotor inside the operation portion; and a restriction member that is disposed to be able to contact the rotor supported by the support member and restricts rotation operation centered at a central axis of the shaft.

Example 2. The insertion instrument according to Example 1, wherein the rotor has a concave surface at an outer surface, and the restriction member protrudes inside the concave surface from the support member toward a center of the rotor.

Example 3. The insertion instrument according to Example 2, wherein the restriction member has a shape with which the restriction member contacts the concave surface and restricts rotation of the rotor in a direction about the central axis of the shaft but does not interfere with rotation of the rotor in a direction other than the direction about the central axis of the shaft.

Example 4. The insertion instrument according to Example 3, wherein the restriction member is a plate material having a curved surface that contacts the concave surface.

Example 5. The insertion instrument according to Example 4, wherein the restriction member has a tapered shape toward the center of the rotor.

Example 6. The insertion instrument according to Example 1, wherein the bending portion can bend in an up-down direction, a right-left direction orthogonal to the up-down direction, and a direction as a combination of the up-down direction and the right-left direction when the wire fixation member pulls the wire.

Example 7. The insertion instrument according to Example 6, wherein the wire fixation member is provided at a position different from the rotor in a longitudinal direction of the shaft, and the wire extends from three places on the wire fixation member toward inside of the bending portion.

Example 8. The insertion instrument according to Example 6, wherein the wire fixation member is provided at a same position as the rotor in a longitudinal direction of the shaft, and the wire extends from four places on the wire fixation member toward inside of the bending portion.

Example 9. The insertion instrument according to Example 1, wherein the operation portion includes a first outer shell provided with the support member, and a second outer shell bonded to the first outer shell and forming an outer surface of the operation portion.

Example 10. The insertion instrument according to Example 9, wherein the restriction member is provided at least one of the first outer shell or the second outer shell.

Example 11. The insertion instrument according to Example 9, wherein the support member and the restriction member are integrally formed only with the first outer shell.

Example 12. The insertion instrument according to Example 1, further comprising a lock mechanism that fixes operation of the rotor at a predetermined rotational position by adding friction to the rotor through an operation from outside of the operation portion.

Example 13. The insertion instrument according to Example 1, wherein the wire fixation member includes a plurality of fixation portions for changing pulled amounts of the respective wire in plurality in accordance with inclination operation of the lever.

Example 14. The insertion instrument according to Example 13, wherein the wire fixation member includes the plurality of fixation portions can selectively adjust fixation positions of the respective wire in plurality.

Example 15. The insertion instrument according to Example 1, wherein the support part includes a plurality of lock lugs provided at any one of the first outer shell and the second outer shell, and the lock lugs elastically deform and support the rotor to an inner surface of the support part.

Example 16. The insertion instrument according to Example 1, wherein the insertion instrument is intended for a urinary organ.

Example 17. The insertion instrument according to Example 1, wherein the insertion instrument is a single-use instrument that is discarded once inserted into an examination target body for a single examination.

What is claimed is:

1. An insertion instrument, comprising:

an insertion portion including a bending portion provided at a distal end side of the insertion portion;

a first wire provided in the insertion portion; and an operation portion provided at a proximal end side of the insertion portion, wherein the operation portion includes a bending operation unit, wherein the bending operation unit includes:

a lever having a central shaft defining a central axis, a rotor coupled to the lever, a wire attachment surface to which the first wire is attached, wherein an inner surface of the operation portion includes a receiver body and a restriction body, wherein the receiver body supports the rotor for rotation about the central axis and for movement of the lever from a neutral position to an inclined position, where, in the inclined position, the central shaft is inclined relative to the central shaft in the neutral position, wherein movement of the lever from the neutral position to the inclined position pulls the first wire to bend the bending portion, wherein the restriction body restricts a portion of the rotation of the rotor about the central axis, wherein the operation portion includes:

a first outer shell forming a first portion of an outer surface of the operation portion, and a second outer shell bonded to the first outer shell and forming a second portion of the outer surface of the operation portion, and wherein at least one of the first outer shell and the second outer shell includes the restriction body.

2. The insertion instrument according to claim 1, wherein the rotor has a body including an outer peripheral surface and a recess, and wherein the restriction body extends into the recess.

3. The insertion instrument according to claim 2, wherein the restriction body extends toward a center of the rotor.

4. The insertion instrument according to claim 2, wherein the recess extends in a circumferential direction of the rotor a first distance, the outer peripheral surface of the body extends in the circumferential direction of the rotor a second distance, and the first distance is equal to or less than the second distance.

5. The insertion instrument according to claim 4, wherein the first distance is equal to or less than half the second distance.

6. The insertion instrument according to claim 2, wherein a surface of the receiver body is curved, and wherein the restriction body has a shape of a plate having a curved peripheral surface that contacts the surface of the receiver body.

7. The insertion instrument according to claim 6, wherein, in a plane perpendicular to the central axis, the restriction body has a wedge shape.

8. The insertion instrument according to claim 2, wherein the wire attachment surface has a shape of a plate, and wherein a planar surface of the wire attachment surface is orthogonal to the central axis.

9. The insertion instrument according to claim 1, further comprising:

a second wire provided inside of the insertion portion and attached to the wire attachment surface; and a third wire provided inside of the insertion portion and attached to the wire attachment surface, and wherein the first wire, the second wire and the third wire extend from the wire attachment surface to the bending portion.

10. The insertion instrument according to claim 9, wherein the lever, the rotor, and the wire attachment surface are arranged along the central axis with the rotor positioned between the lever and the wire attachment surface.

11. The insertion instrument according to claim 9, further comprising:

a fourth wire provided inside of the insertion portion and attached to the wire attachment surface, wherein the wire attachment surface is provided on an outer peripheral surface of the rotor, and wherein each of the first wire, the second wire, the third wire and the fourth wire extend from the wire attachment surface to the bending portion.

12. The insertion instrument according to claim 1, wherein at least one of the first outer shell and the second outer shell includes the receiver body.

13. The insertion instrument according to claim 12, wherein the receiver body includes a plurality of lock lugs, and wherein the lock lugs support an outer peripheral surface of the rotor.

14. The insertion instrument according to claim 1, wherein the bending operation unit further comprises a pressure adjustment mechanism having a pressing surface, and wherein the pressure adjustment mechanism is configured to adjust a friction contact between the pressing surface and the receiver body.

15. The insertion instrument according to claim 14, wherein the friction contact is sufficient to prevent the rotation of the rotor.

16. The insertion instrument according to claim 1, wherein the wire attachment surface includes a tapered hole to which the first wire is attached.

17. The insertion instrument according to claim 1, wherein the receiver body supports an outer peripheral surface of the rotor.

18. The insertion instrument according to claim 1, wherein the insertion instrument is configured for insertion into a urinary organ.

19. The insertion instrument according to claim 1, wherein a surface of the receiver body is curved, and wherein an outer surface the rotor has a spherical shape contacting the surface of the receiver body.

20. An insertion instrument, comprising:

an insertion portion including a bending portion provided at a distal end side of the insertion portion;

a first wire provided in the insertion portion; and an operation portion provided at a proximal end side of the insertion portion, wherein the operation portion includes a bending operation unit, wherein the bending operation unit includes:

a lever having a central shaft defining a central axis, a rotor coupled to the lever, a wire attachment surface to which the first wire is attached, wherein an inner surface of the operation portion includes a receiver body and a restriction body, wherein the receiver body supports the rotor for a rotation operation and for an inclination operation, wherein the rotation operation is rotation about the central axis and the inclination operation is movement of the lever from a neutral position to an inclined position, where, in the inclined position, the central shaft is inclined relative to the central shaft in the neutral position, wherein movement of the lever from the neutral position to the inclined position pulls the first wire to bend the bending portion, wherein the restriction body restricts the rotation operation centered at the central axis and allows the inclination operation in all directions, wherein the operation portion includes:

a first outer shell forming a first portion of an outer surface of the operation portion, and a second outer shell bonded to the first outer shell and forming a second portion of the outer surface of the operation portion, and wherein at least one of the first outer shell and the second outer shell includes the restriction body.

* * * * *